US006287839B1

(12) United States Patent
Jones et al.

(10) Patent No.: US 6,287,839 B1
(45) Date of Patent: Sep. 11, 2001

(54) CELLULASE PRODUCING ACTINOMYCETES, CELLULASE PRODUCED THEREFROM AND METHOD OF PRODUCING SAME

(75) Inventors: Brian E. Jones, Leidschendam; Wilhelmus A. H. Van Der Kleij; Piet Van Solingen, both of Naaldwijk, all of (NL); Walter Weyler, San Francisco, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/321,981

(22) Filed: May 28, 1999

Related U.S. Application Data

(63) Continuation-in-part of application No. 09/104,308, filed on Jun. 24, 1998, now Pat. No. 6,187,577, which is a continuation-in-part of application No. 08/974,042, filed on Nov. 19, 1997, now abandoned.

(51) Int. Cl.[7] ................................................... C12N 9/42
(52) U.S. Cl. ........................... 435/209; 435/263; 426/61; 510/392
(58) Field of Search ................................... 435/209, 263; 510/392; 426/61

(56) References Cited

U.S. PATENT DOCUMENTS 5,792,641 * 8/1998 Schulein et al. ..................... 435/209

FOREIGN PATENT DOCUMENTS

| WO 96 34092 A | 10/1996 | (WO) . |
| WO 96 34108 A | 10/1996 | (WO) . |
| WO 97 27363 A | 7/1997 | (WO) . |
| WO 99 31255 A | 6/1999 | (WO) . |

OTHER PUBLICATIONS

Wilson, D.B. (1992) Crit. Rev. Biotechnol. 12(1/2), 45–63.*
Garda, A. L. et al., "Two genes encoding an endoglucanase and a cellulose–binding protein are clustered and co–regulated by a TTA codon in *Streptomyces halstedii*," *Biochem. J.*, V. 342, Jun. 1, 1997, pp. 403–411.
Lao, G. et al., DNA sequences of three beta–1,4–endoglucanase genes from Thermomonospora fusca:, *Journal of Bacteriology*, V. 173, Jun. 1, 1991, pp. 3397–3407.
Nakai, R. et al., "Cloning and nucleotide sequence of a cellulase gene cas–A from an alkalophilic Streptomyces strain," *Gene*, V. 65, N. 2, 1988, pp. 229–238.
Nakai, R. et al., "Purification and properties of cellulases fron an alkalophilic Streptomyces strain", *Agricultural and Biological Chemistry*, V. 51, N. 11, 1987, pp. 3061–3065.
Perito, B. et al., "Characterization and sequence analysis of a Streptomyces rochei A2," *Gene*, 148, 1994, pp. 119–124.
Shikata, S. et al., "Alkaline Cellulases for Laundry Detergents: Production by Alkalophilic Strains of Bacillus and some Properties of the Crude Enzymes," *Agricultural and Biological Chemistry*, V. 54, N. 1, Jan. 1, 1990, pp. 91–96.
Wittman, S., et al., "Purification and characterization of the CelB endoglucanase from Streptomyces lividans 66 and DNA sequence of the encoding gene," *Applied and Environmental Microbiology*, V. 60, N. 5, 1994, pp. 1701–1703.
Theberge, M. et al., "Purification and characterization of an endoglucanase from Streptomyces lividans 66 and DNA sequence of the gene," *Appled and Environmental Microbiology*, V. 58, N. 3, Mar. 1992 pp. 815–820.
PCT Search Report, PCT/US99/11971 (1999).

* cited by examiner

Primary Examiner—Charles L. Patterson, Jr.
(74) *Attorney, Agent, or Firm*—Genencor International

(57) ABSTRACT

A novel cellulase composition is provided which is predicable by an Actinomycete. The cellulase has an approximate calculated molecular weight of 36 kD and has a pH optimum at 40° C. of 8 and at 60° C. of 7. Also provided is a DNA encoding said cellulase, a method for producing the cellulase and applications thereof.

12 Claims, 18 Drawing Sheets

MRSHPRSATMTVLVVLASLGALLTAAAPAQANQQICDRYGTTTIQDRYVVQNNRWGTSATQCIN
VTGNGFEITQADGSVPTNGAPKSYPSVYDGCHYGNCAPRTTLPMRISSIGSAPSSVSYRYTGNG
VYNAAYDIWLDPTPRTNGVNRTEIMIWFNRVGPVQPIGSPVGTAHVGGRSWEVWTGSNGSNDVI
SFLAPSAISSWSFDVKDFVDQAVSHGLATPDWYLTSIQAGFEPWEGGTGLAVNSFSSAVNAGGG
NGGTPGTPAACQVSYSTHTWPGGFTVDTTITNTGSTPVDGWELDFTLPAGHTVTSVWNALISPA
SGAVTARSTGSNGRIAANGGTQSFGFQGTSSGAGFTAPAGARLNGTSCTVR

FIG._1

ATGAGATCCCATCCCCGCTCCGGCGACGATGACCGTCCTCGTCGTCCTCGCCTCCTCGGCG
CGCTGCTCACCGCAGCGGCTCCCGCCCAGGCGAACCAGCAGATCTGCGACCGCTACGGCA
CCACCACGATCCAAGGACCGGTACGTGTGCAGAACAACCGCTGGGCACCAGCGCCACCC
AGTGCATCAATGTGACCGGCAACGGTTTCGAGATCACCCAGGCCGACGGTTCGGTGCCGAC
CAACGGCGCCCCGAAGTCCTATCCCTCGGTTCTACGACGGCTGCCACTACGGCAACTGCGC
GCCCCGCACGACGCTGCCCATGCGGATCAGCTCGATCGGCCAGCGCCAGCAGTGTCTC
CTACCGCTACACCGGCAACGGCGTCTACAACGCCGGTACGACATCTGGCTGGACCCGACA
CCCCGCACCAAGGGGTGAACCGGACCGAGATCATGATCTGGTTCAACCGGGTCGGCCCG
GTCCAGCCCCATCGGTTCGCCGGTGCGGCAACGTCGGCCACGTCGGCCGCCAGCTGGGAGGT
GTGGACCGGCAGCAACGGTTCGAACGACGTGATCTCCTTCCTGGCGCCGTCCGCGATCAG
CAGCTGGAGCTTCGACGTCAAGGACTTCGTCGACCAGGCCGTCAGCCACGGCCTGGCCAC
CCCGGACTGGTACCTCACCAGCATCCAGGCGGGCTTCGAGCCGGGGGAGGCGCACCG
GTCTGGGCCGTGAACTCGTTCTCTCCGCAGGTCTCCTACAGCGCCACCCGTGGGCGCTTCA
CGGGGACACCGGCACCACCATTACCGGCTCCACCAGCGTGTGAACGCGCTGATCAGCCCGCCTC
CCGTGACACCACCACCCGCGGTCACCACGCAGGGCACCTTCCAGGGCACCTCCAGCGGGAGCTGGGAACTGACTT
CACCCTCCCCGGCGGCCACTGGACGGCCGATCGCGCCAACGGCGGGA
GGGCGCGGTCACGCACGCAGGGCACCTTCCAGGGCACCTCCAGCGGGAGCGGGTCACCGCAACGGCGGGA
CCCAGTCCTTCGGTTCGGTTCCAGGGGAGCGGGGTTCACCGCCACCGGCGGGG
CCCGGCTCAAGGGCCACCTCCTGCACAGTGAGATGA

FIG._2

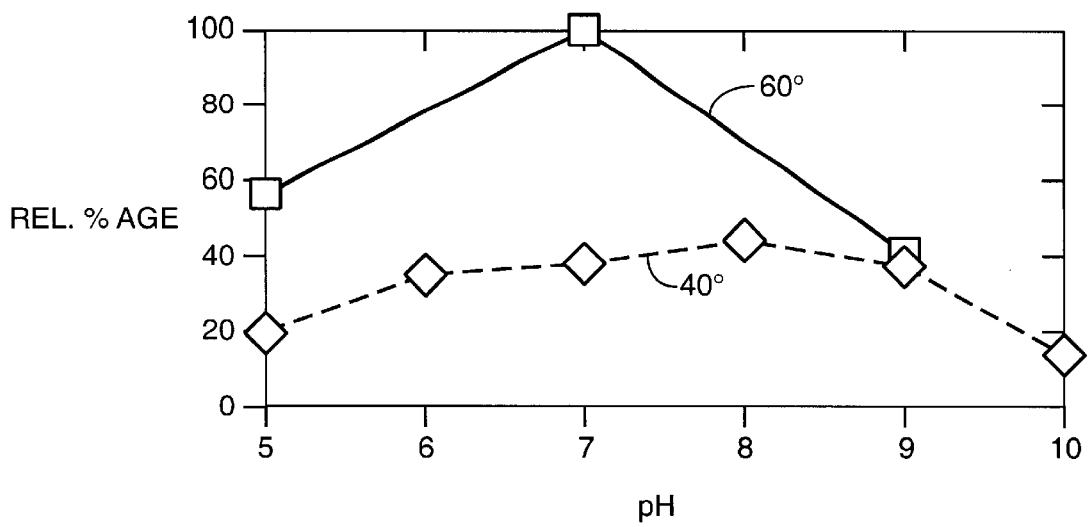

FIG._3

```
                GAACGCTGGCGGCGTGCTTAACACATGCAAGTCGAACGATGAAG
CCGCTTCGGTGGTGGATTAGTGGCGAACGGGTGAGTAACACGTGGGCAATCTGCCCTGCA
CTCTGGGACAAGCCCGGGAAACTGGGTCTAATACCGGATA-TGACACACGACCGCATGGT
CTGTGTGTGGAAAGCTCCGGCGGTGCAGGATGAGCCCGCGGCCTATCAGCTTGTTGGTGG
GGTAATGGCCTACCAAGGCGACGACGGGTAGCCGGCCTGAGAGGGCGACCGGCCACACTG
GGACTGAGACACGGCCCAGACTCCTACGGGAGGCAGCAGTGGGGAATATTGCACAATGGG
CGAAAGCCTGATGCAGCGACGCCGCGTGAGGGATGACGGCCTTCGGGTTGTAAACCTCTT
TCAGCAGGGAAGAAGCTTTCGGGTGACGGTACTGCAGAAGAAGCACCGGCTAACTACGTG
```

FIG._6

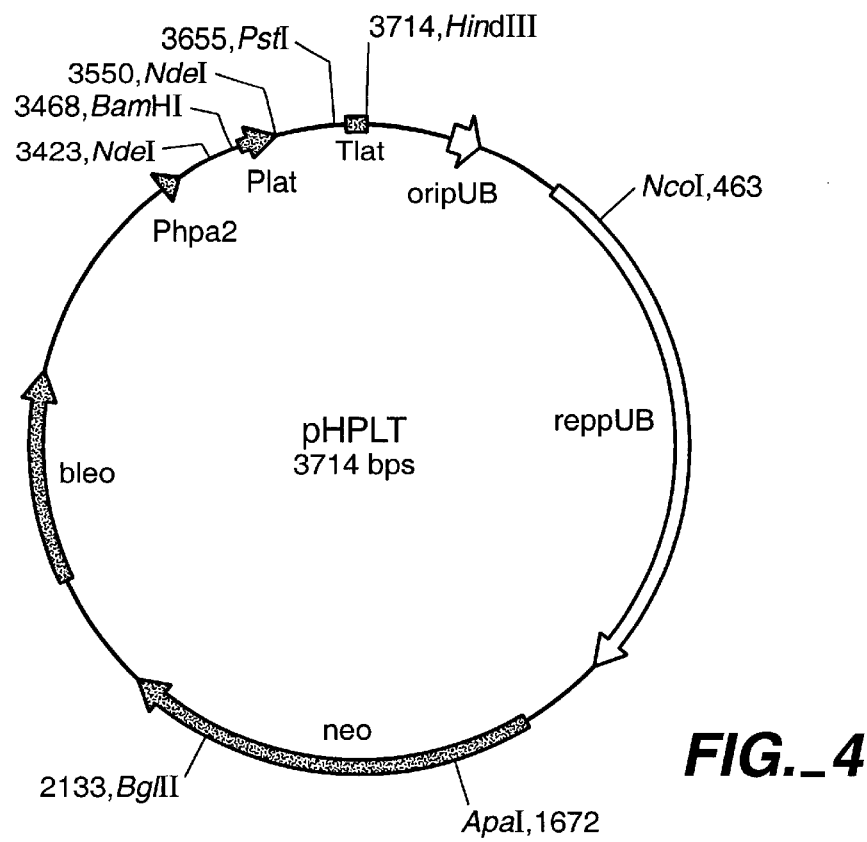
FIG._4
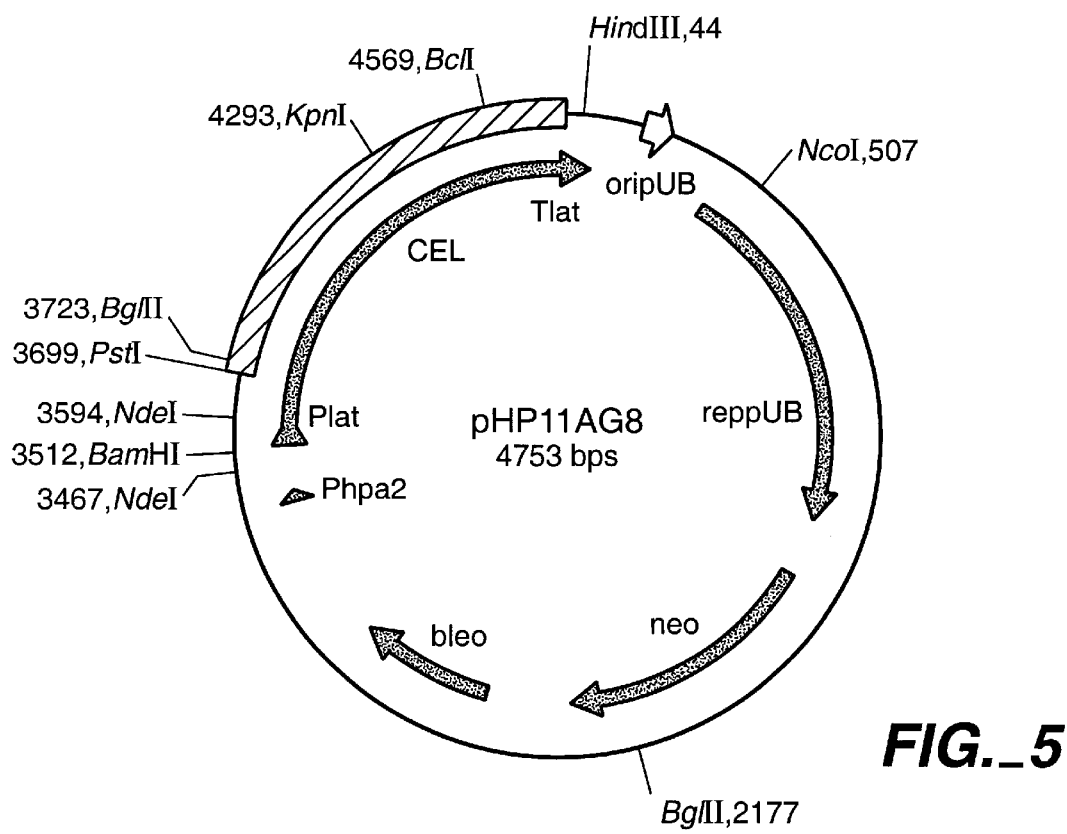
FIG._5

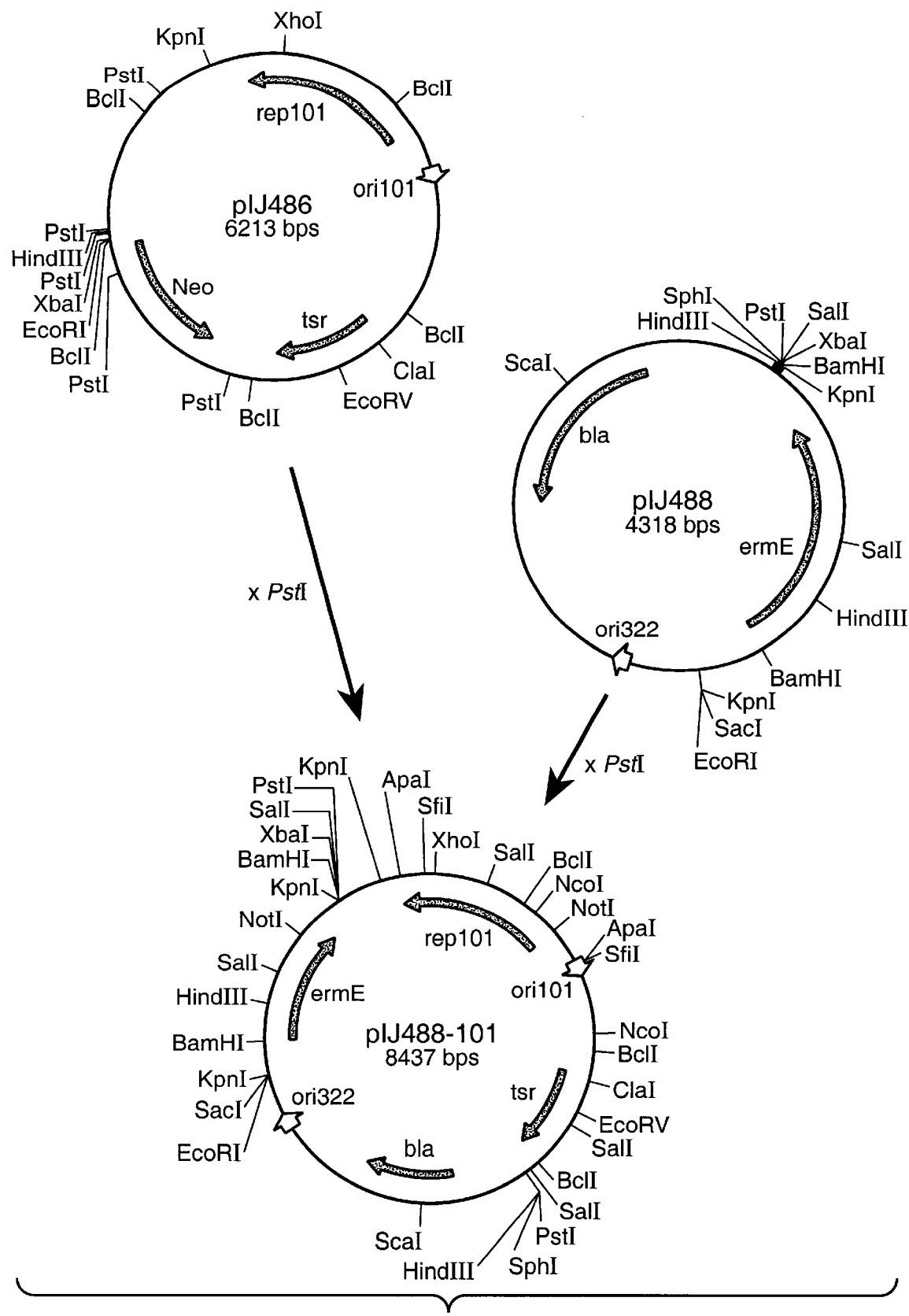
FIG._7

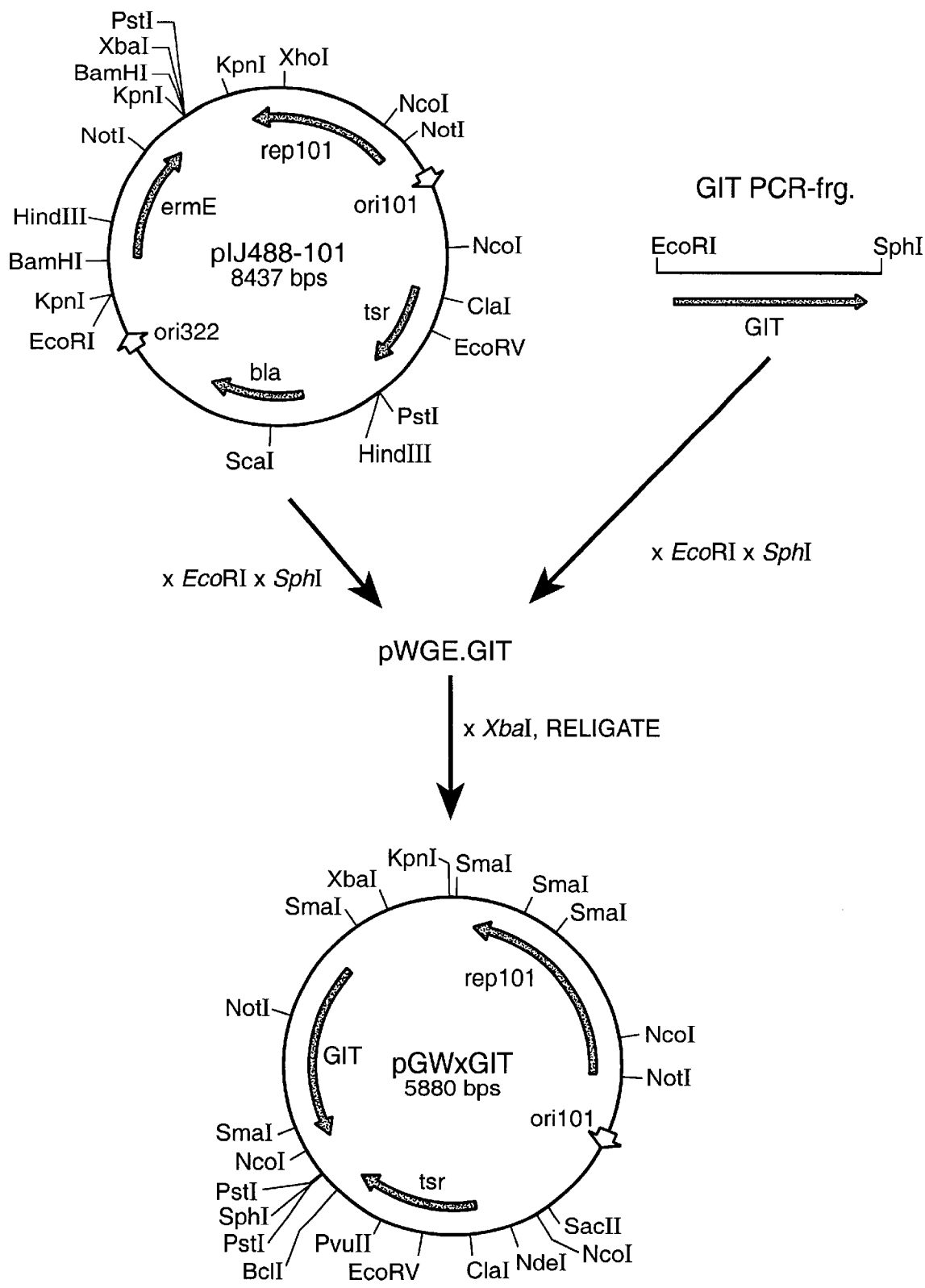
FIG._8

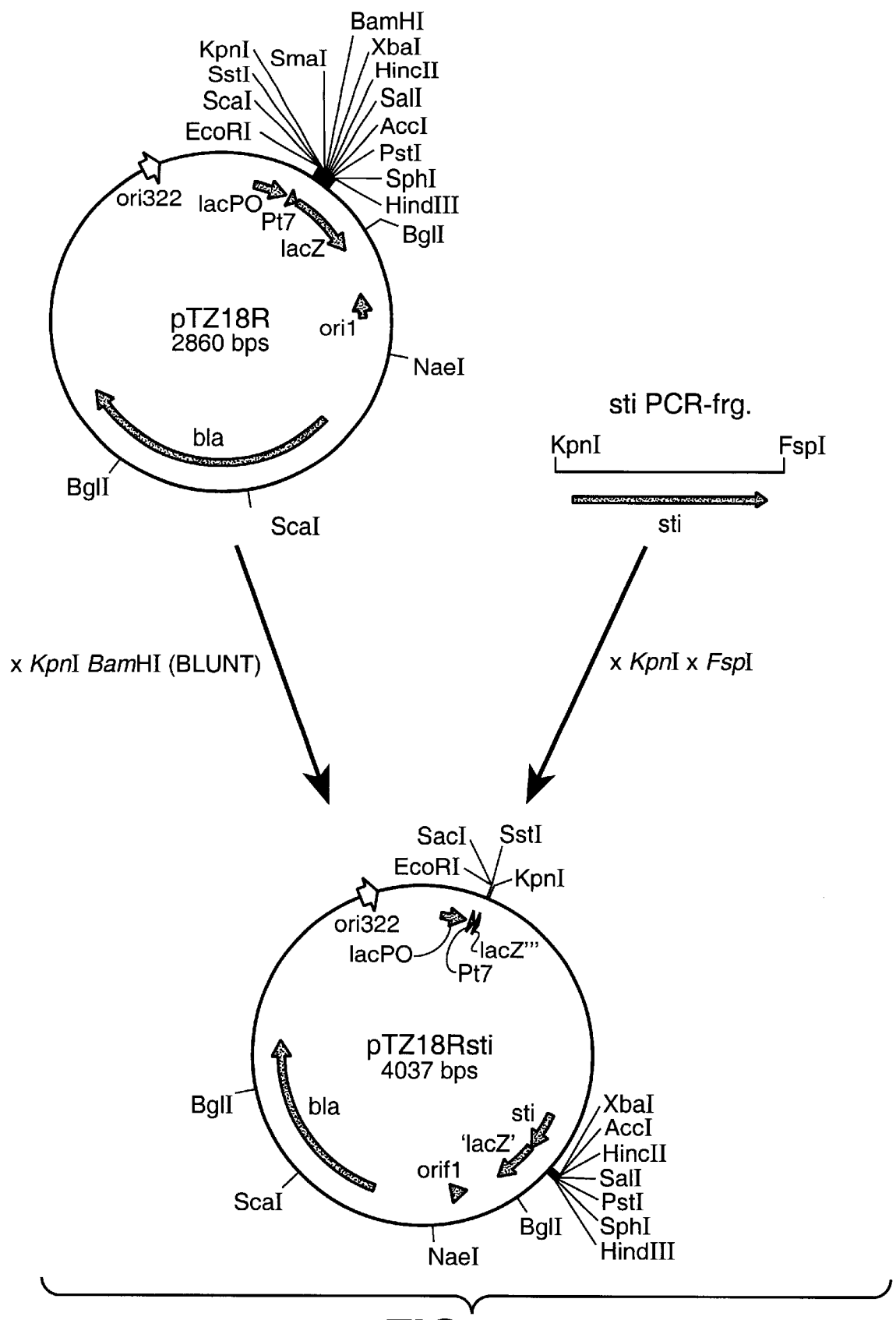
FIG._9

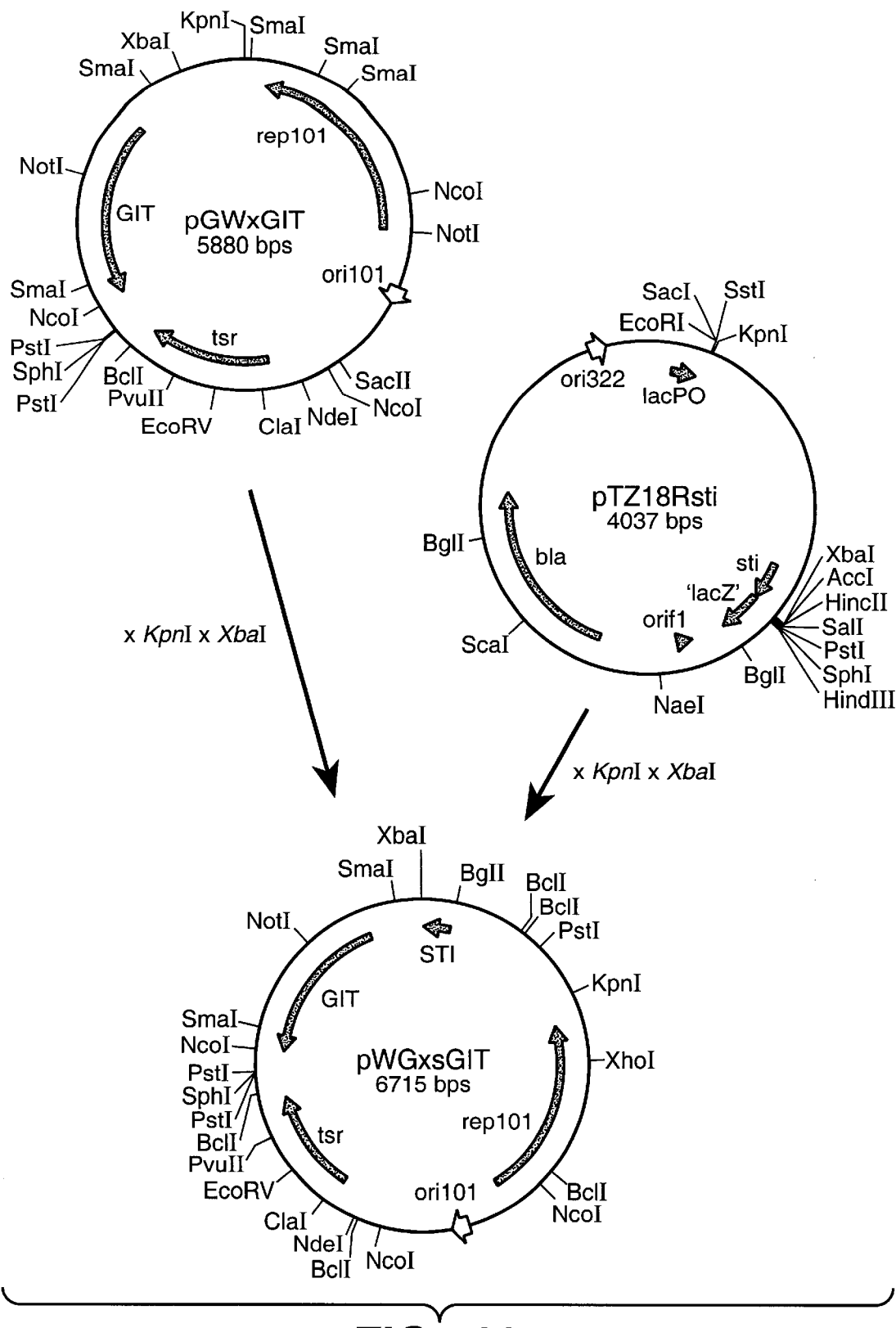
FIG._10

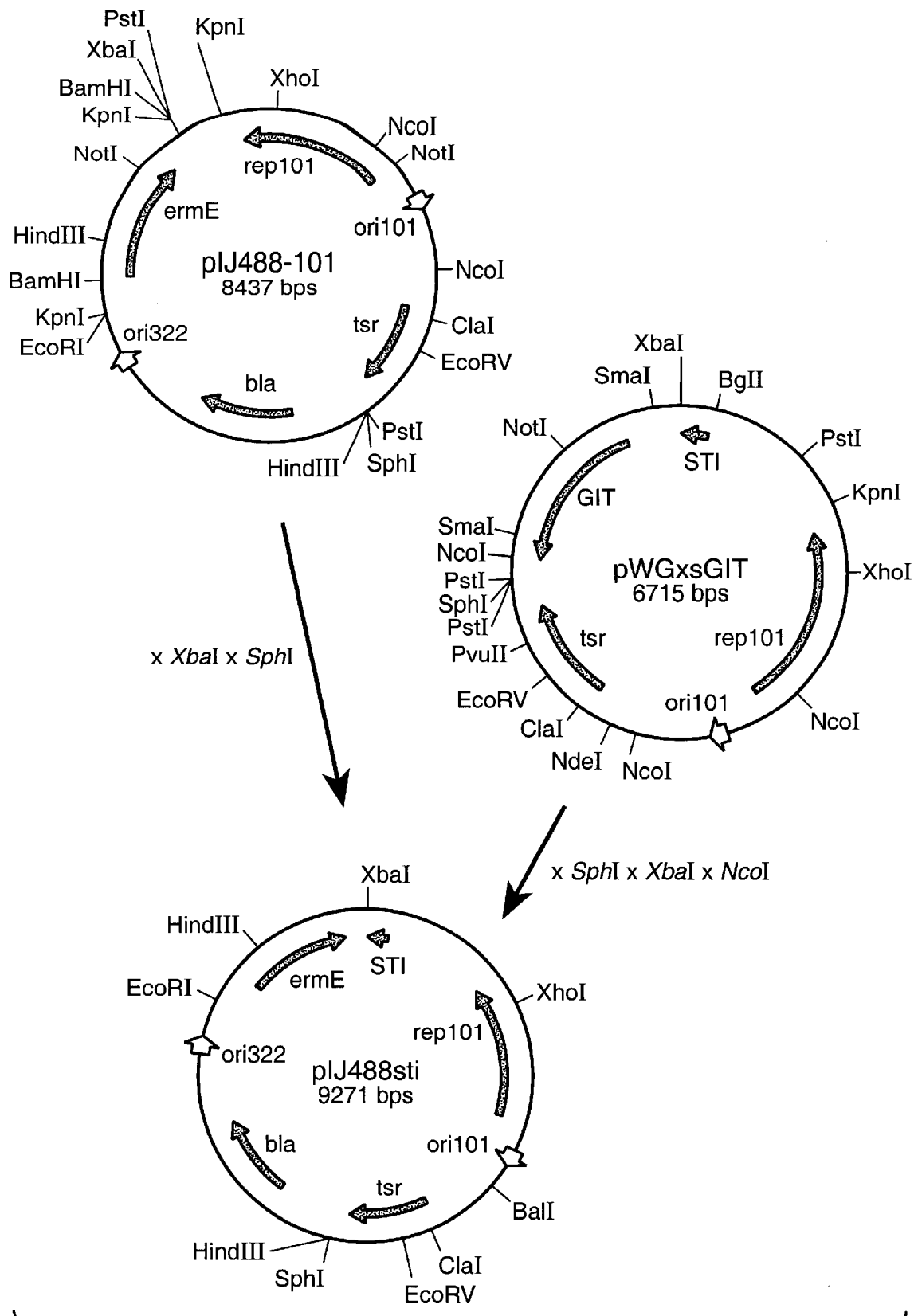
FIG._11

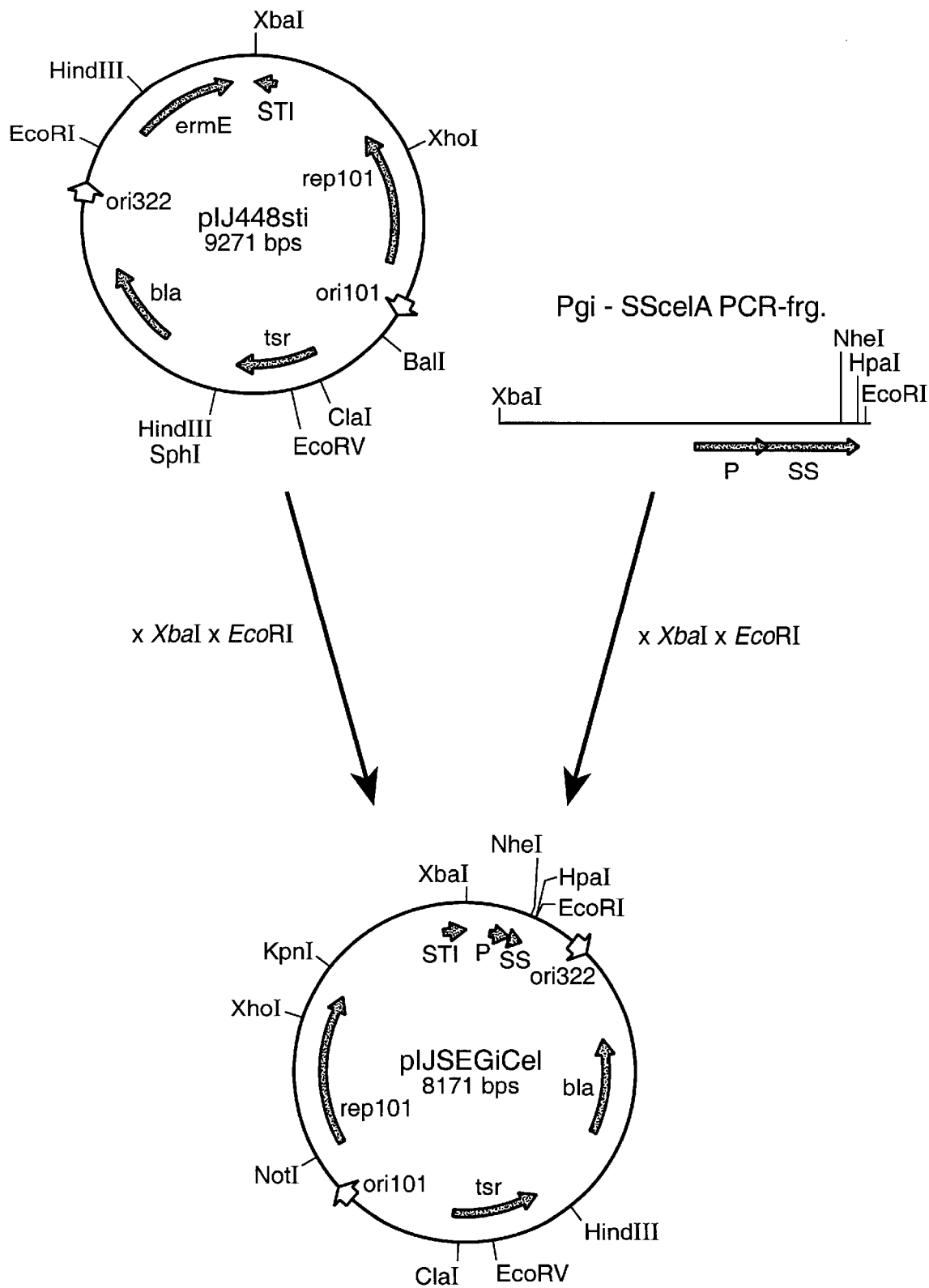
FIG._12

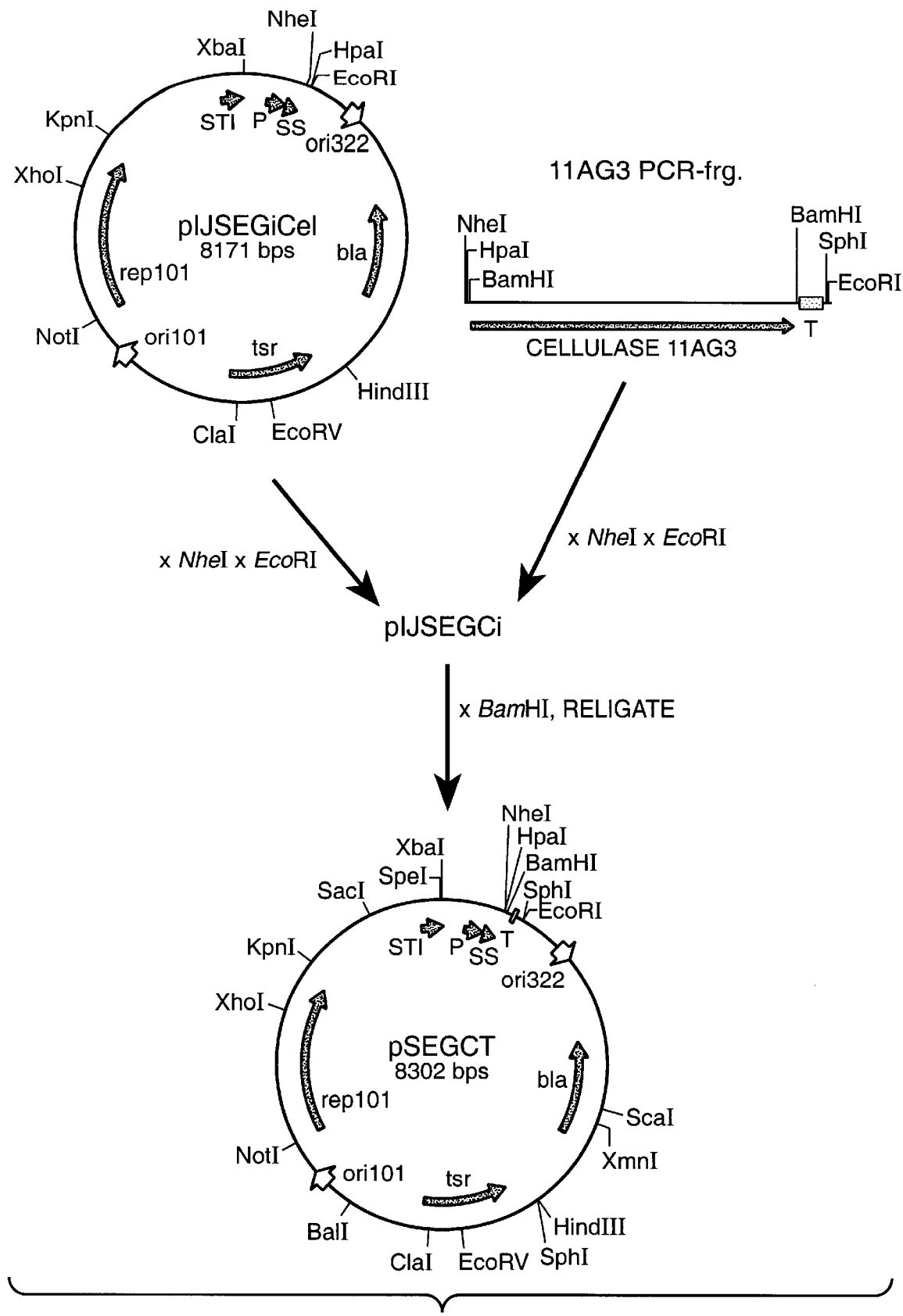
FIG._13

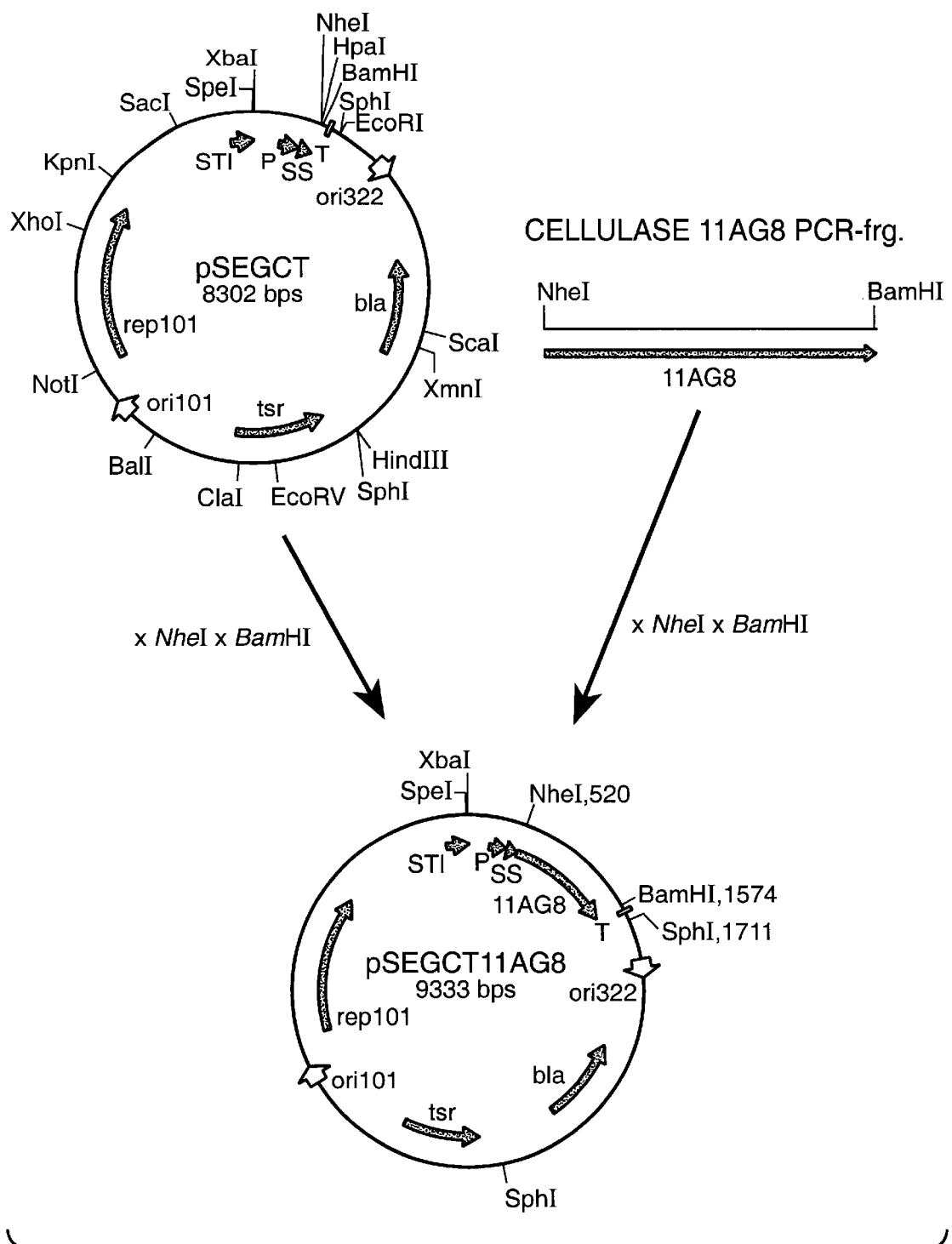
FIG._14

FIG._15

DNA sequence of GI promoter, CelA signal sequence, 11AG8 mature and 11AG3 terminator.

CTAGAGTCGACCACGCAGGCCCGCCAGGTAGTCGACGTTGATCTCGCAGCCGAGCCCGGCGACCGGCGGCGCTGAGCGC
GAGGCCGACGGGCCGGACGGCCCGGCCACCCGGGTGCGGGTCGAGTTCGGTGAGCAGCCACCCGGCGATCAGGTCGT
CGACGAGCGCGAGACGGTGGCCCGGGTGACGGCGGCAACTCCCGCGGGAGAGCCGATCTGTCGTGTT
GCCACGGTATGCAGCGCCCCTTGACAATGCCACATCCTGAGCGCGCTCGACACTGTCGGAACGGCACTGAACGAGAAGTCAG
GCGAGCCGTCACGCCCTTGGGAGCGCTGTCGACCATCGCGTTGTGTCCGTTGTGTCCGCTAGCGCGGCACAGGCCACCAGATCTGC
GTAACCATGGGCTTCGGACCGGCGTGTCCGATCGTCGGCCTGACTCGTGGCTGCAGAACAACCGCTGGGCGCACCAGCGCCACCCAGTCGC
CTGCTCGCGGACCGGCGTGTCGATCGTCGGCCTGACTCGTGGCTGCAGAACAACCGCTGGGCGCACCAGCGCCACCCAGTCGC
ACCGCTACGGCCACCACGATCAGGACGGTTTCGAGATACACCCAGCCGACGGTTCGGTGCCGACCAACGGCGCGGATCAGCTCGATCGGCAGCGCGC
AATGTGACCGGCAACGGTTTCGACTACGGCCAACTCGCGCGCCCGGATCAGCTCGATCGGCAGCGCGC
GGTCTACGACGCTGCCACTACGCTACAACGCCAACGGCGTCTACAACCGCCGTATCGCGATCTCTGGCTGACCCGCGACACCCCGC
CCAGCAGTGTCTCCTACCGCTACAACGCCAACGGCGTCTACAACCGCCGTATCTGGCTGACCCGCGACACCCCGC
ACCAACGGGTGAACCGGACCGAGATCATGATCTGGTTCAACCGGGTCGGCCCCATCGGTTCGCCGGTCGG
CCTCCGGGATCAGCAGCTGGAGCTTCGACGTCAAGGACTTCGTCGACCAGCCGGTGAACGACGTTGATCTCCTTCCTGCGC
TGGTACCTCACCAGCATCCAGGCGGGCTTCGAGCCGTGGAGGGCGCACTCCGCGGCCGTGAACTCGTTCTCCTCCGC
GGTGAACGCCGGGAACGGCGGAACGCGGAACCGAGCACCAATACCGGCTCCACACCCGTCGACGCTGGGAACTGGACTTCACCTC
CCGGCGGTTCACCGTCGACACGGTCGCCAACGCGCCAGTCCTTCGGTTTCCAGGCACTCCAGCGGAACGGGGTTCAACG
TTCAACGGCCGGATCGCCGGCTCAACGGCCCAACCTTCGTCACAGTGAGATGACAATGGGATCCGGAGCGGATCGGCTGACCGG
CACCGGGGAGGAGGAGGCCGGGCCGGGCCGAAAAGTCCGCGGTCCGCTGAATCGCTCCCCGGACGTGGCAGTATC
AGCGCCATGTCCGGCATATCCCAGCCTCCGCATG

Blue: GI Promoter Sequence
Black: CelA Signal Sequence
Red: Mature 11AG8 Sequence
Green: 11AG3 Downstream sequence containing terminator.

Protein sequence of the CelA 11AG8 fusion.

MGFGSAPIALCPLRTRRNALKRLLALLATGVSIVGLTALAGPPAQANQQICDRYGTTTIQDRYVVQNNRWGTSATQCINV
TGNGFEITQADGSVPTNGAPKSYPSVYDGCHYGNCAPRTTLPMRISSIGSAPSSVSYRYTGNGVYNAAYDIWLDPTPRTN
GVNRTEIMIWFNRVGPVQPIGSPVGTAHVGGRSWEVWTGSNGSNDVISFLAPSAISSWSFDVKDFVDQAVSHGLATPDWY
LTSIQAGFEPWEGGTGLAVNSFSSAVNAGGGNGGTPGTPAACQVSYSTHTWPGGFTVDTTITNTGSTPVDGWELDFTLPA
GHTVTSAWNALISPASGAVTARSTGSNGRIAANGTQSFGFGQTSSSGTGFNAPAGGRLNGTSCTVR.

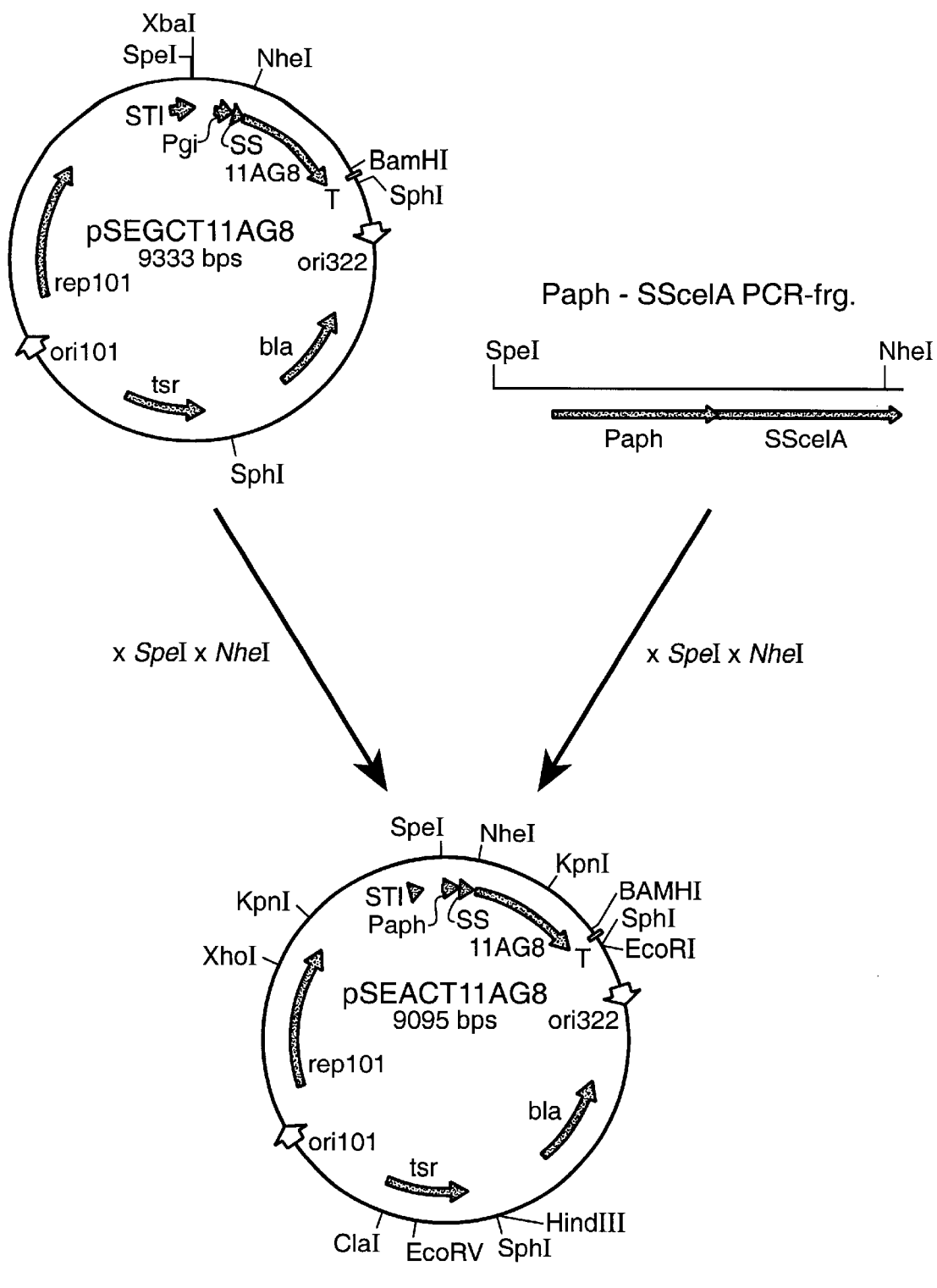
FIG._16

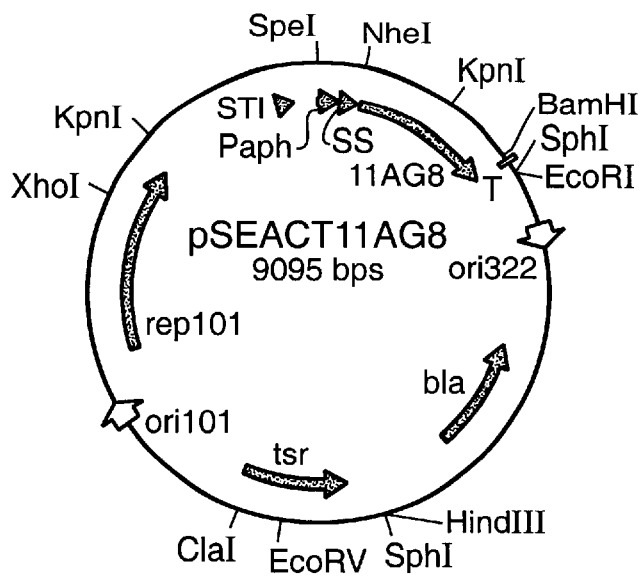
x SphI AND RELIGATE
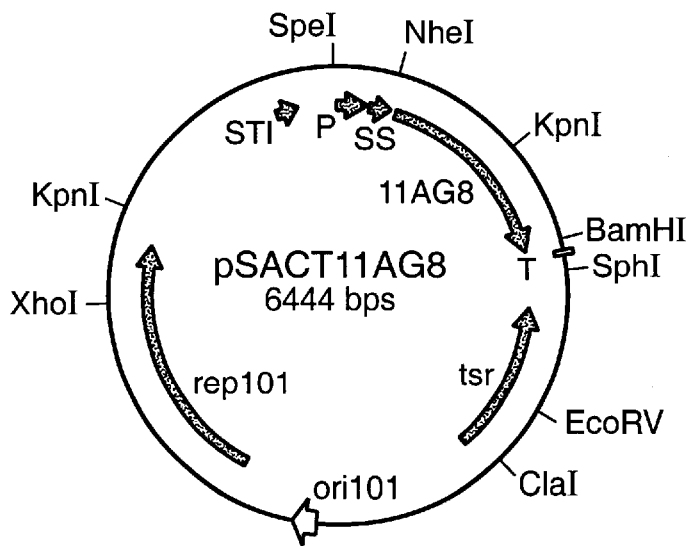
FIG._17

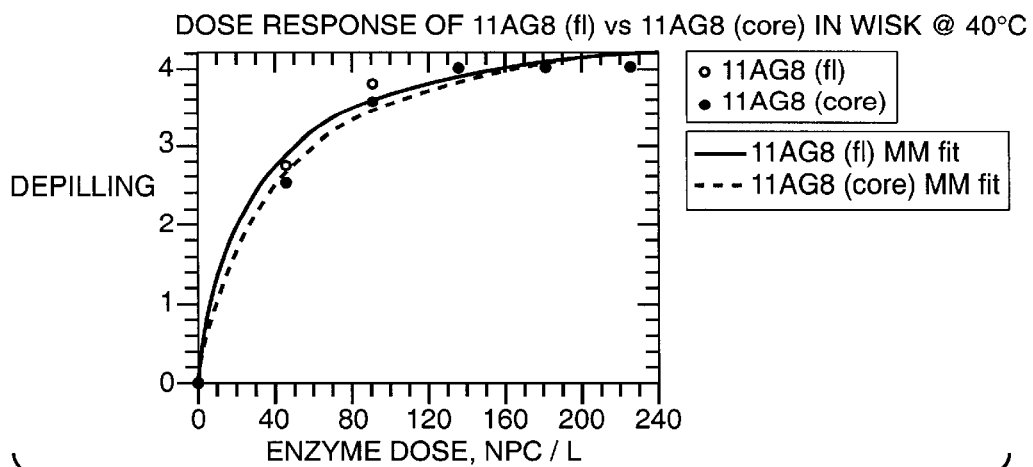
FIG._18a
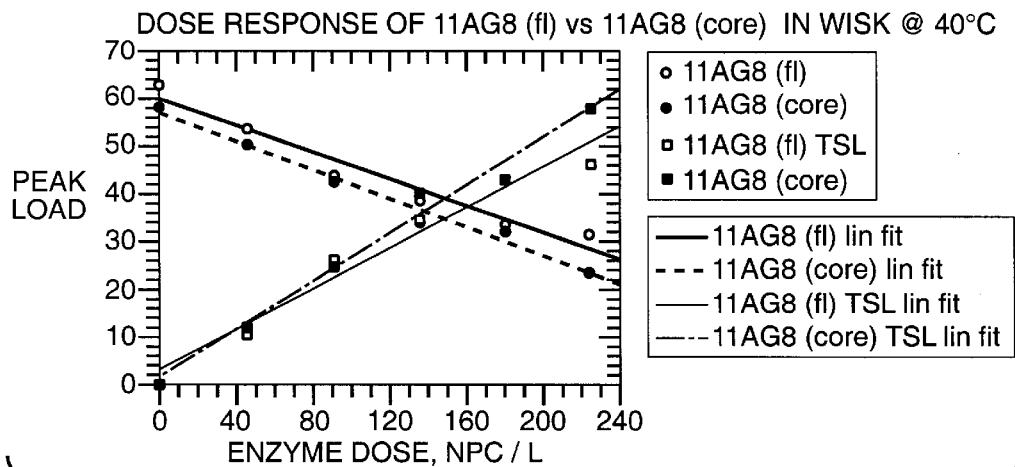
FIG._18b
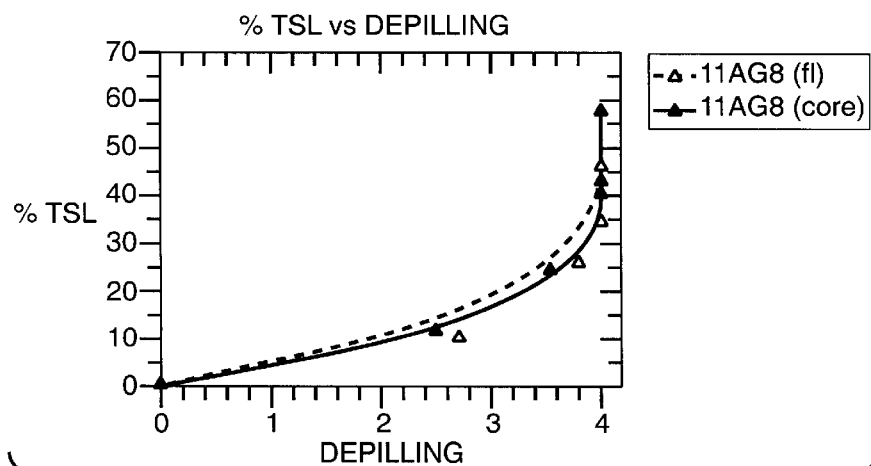
FIG._18c

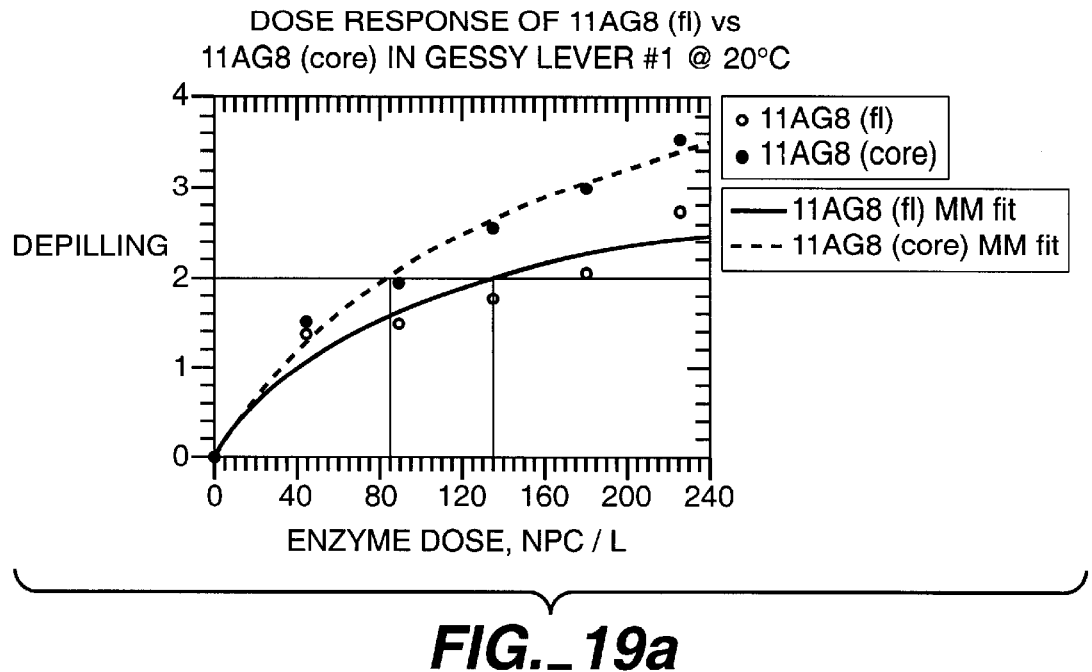
FIG._19a
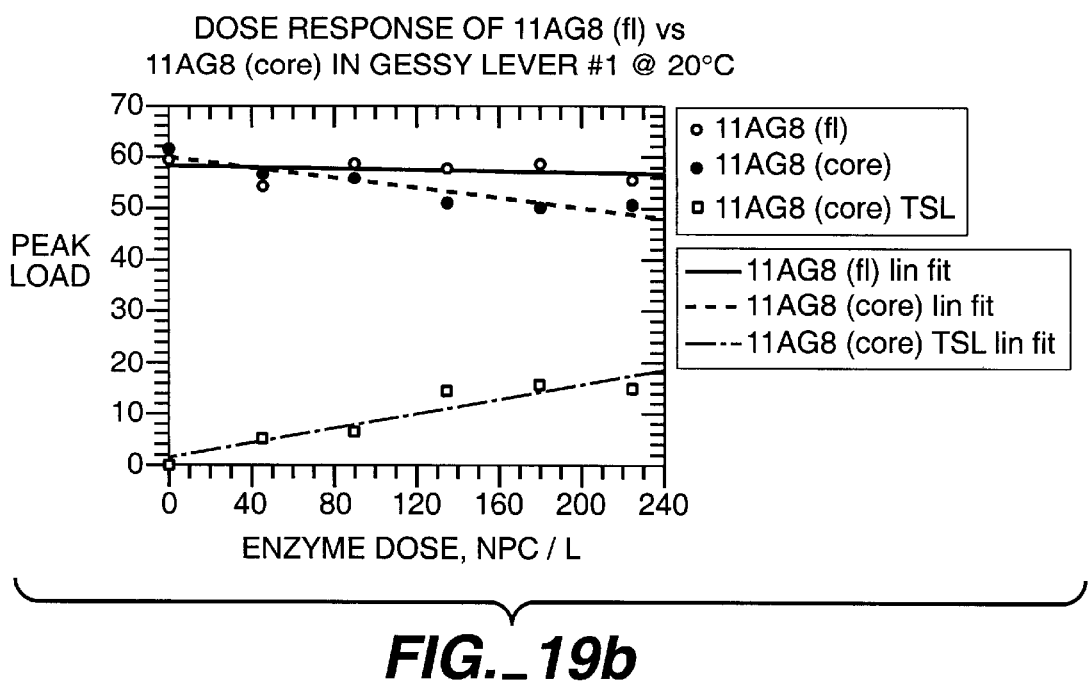
FIG._19b

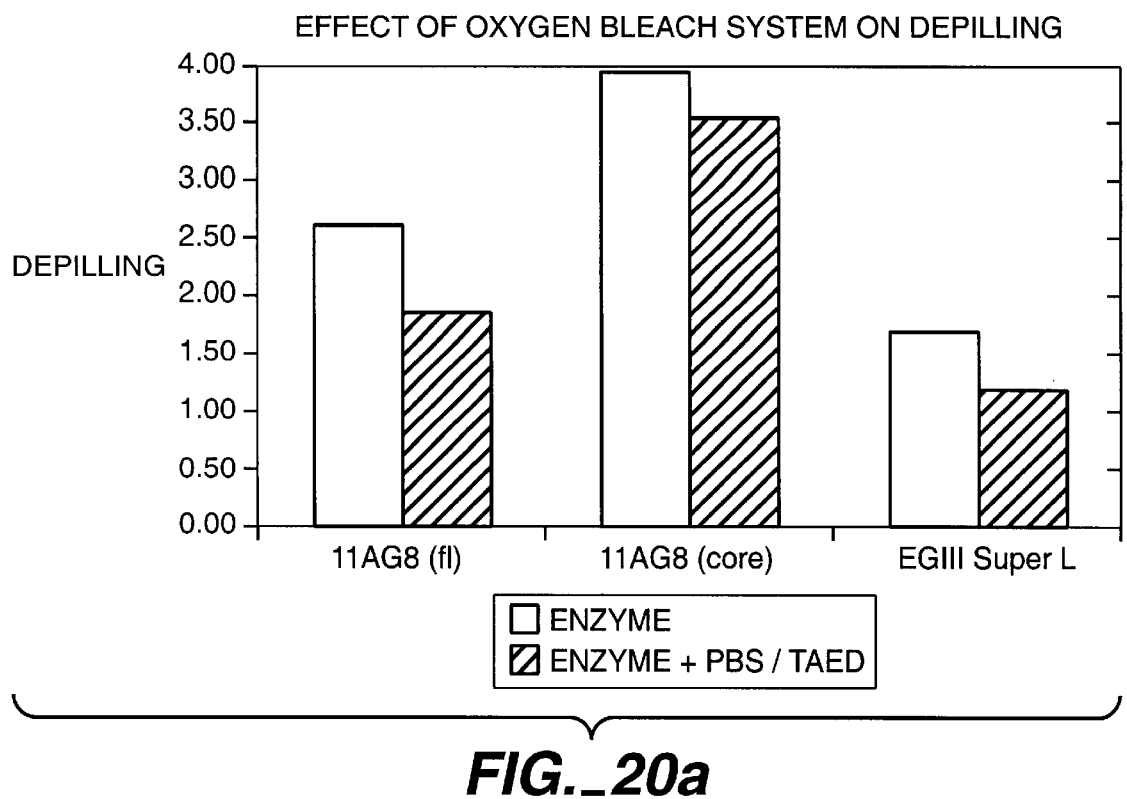
FIG._20a
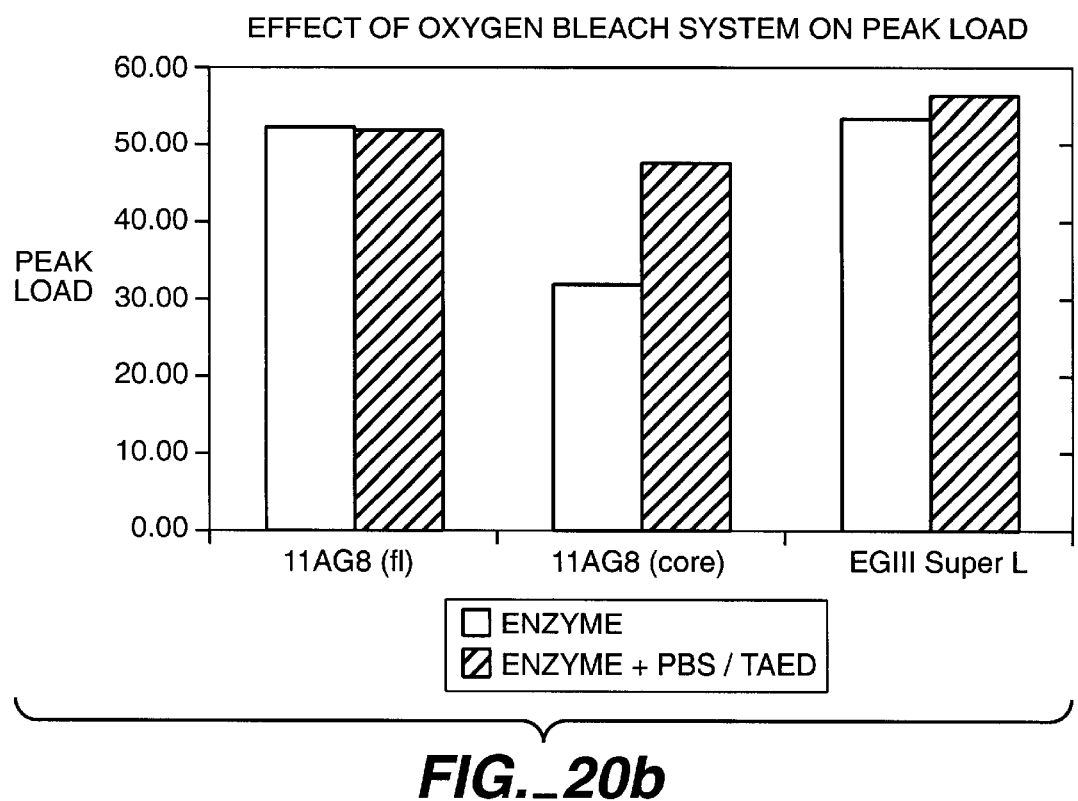
FIG._20b

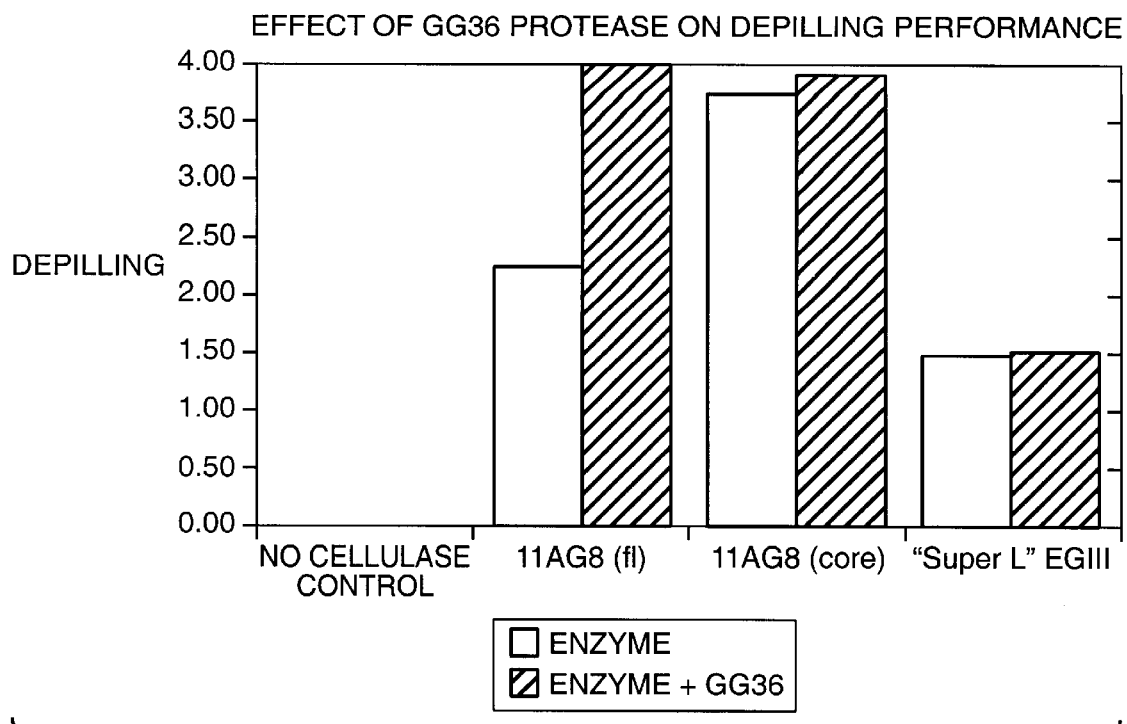
FIG._21a
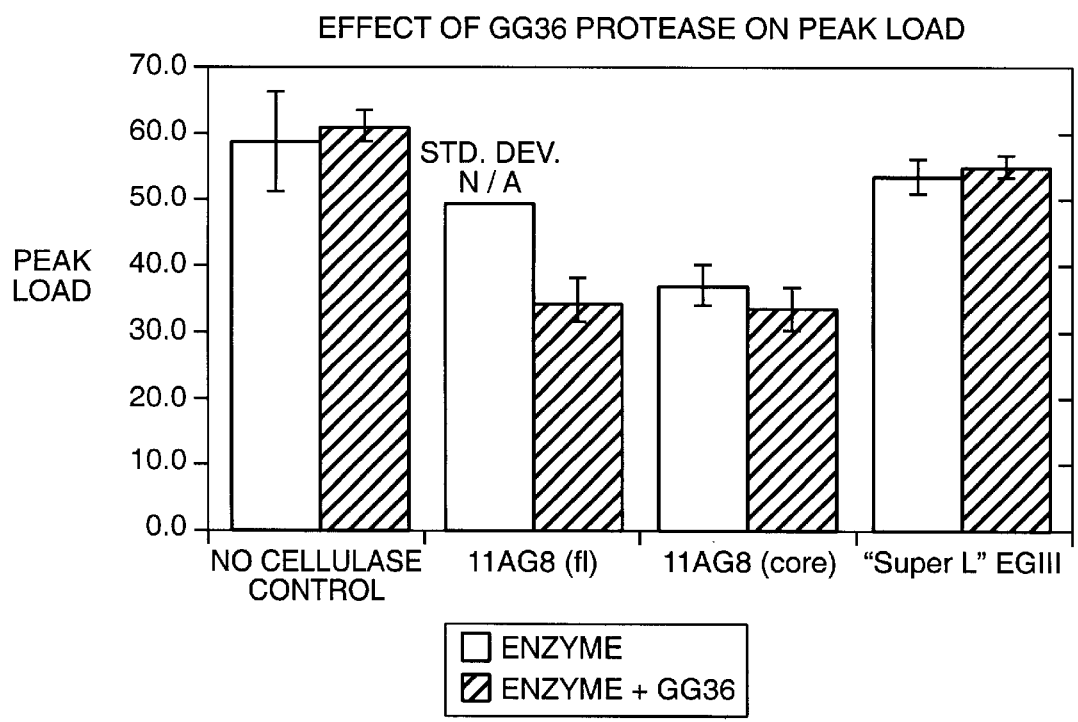
FIG._21b

SEQUENCE LISTING

<160> NUMBER OF SEQ ID NOS: 5

<210> SEQ ID NO 1
<211> LENGTH: 371
<212> TYPE: PRT
<213> ORGANISM: Unknown
<220> FEATURE:
<223> OTHER INFORMATION: Nearest "neighbor" = Streptomycetes thermovebaceous

<400> SEQUENCE: 1

```
Met Arg Ser His Pro Arg Ser Ala Thr Met Thr Val Leu Val Val Leu
1               5                   10                  15

Ala Ser Leu Gly Ala Leu Leu Thr Ala Ala Pro Ala Gln Ala Asn
                20                  25                  30

Gln Gln Ile Cys Asp Arg Tyr Gly Thr Thr Thr Ile Gln Asp Arg Tyr
            35                  40                  45

Val Val Gln Asn Asn Arg Trp Gly Thr Ser Ala Thr Gln Cys Ile Asn
        50                  55                  60

Val Thr Gly Asn Gly Phe Glu Ile Thr Gln Ala Asp Gly Ser Val Pro
65                  70                  75                  80

Thr Asn Gly Ala Pro Lys Ser Tyr Pro Ser Val Tyr Asp Gly Cys His
                85                  90                  95

Tyr Gly Asn Cys Ala Pro Arg Thr Thr Leu Pro Met Arg Ile Ser Ser
                100                 105                 110

Ile Gly Ser Ala Pro Ser Ser Val Ser Tyr Arg Tyr Thr Gly Asn Gly
            115                 120                 125

Val Tyr Asn Ala Ala Tyr Asp Ile Trp Leu Asp Pro Thr Pro Arg Thr
        130                 135                 140

Asn Gly Val Asn Arg Thr Glu Ile Met Ile Trp Phe Asn Arg Val Gly
145                 150                 155                 160

Pro Val Gln Pro Ile Gly Ser Pro Val Gly Thr Ala His Val Gly Gly
                165                 170                 175

Arg Ser Trp Glu Val Trp Thr Gly Ser Asn Gly Ser Asn Asp Val Ile
                180                 185                 190

Ser Phe Leu Ala Pro Ser Ala Ile Ser Ser Trp Ser Phe Asp Val Lys
            195                 200                 205

Asp Phe Val Asp Gln Ala Val Ser His Gly Leu Ala Thr Pro Asp Trp
        210                 215                 220

Tyr Leu Thr Ser Ile Gln Ala Gly Phe Glu Pro Trp Glu Gly Gly Thr
225                 230                 235                 240

Gly Leu Ala Val Asn Ser Phe Ser Ser Ala Val Asn Ala Gly Gly Gly
                245                 250                 255

Asn Gly Gly Thr Pro Gly Thr Pro Ala Ala Cys Gln Val Ser Tyr Ser
```

-continued

```
                  260                 265                 270
Thr His Thr Trp Pro Gly Gly Phe Thr Val Asp Thr Thr Ile Thr Asn
            275                 280                 285

Thr Gly Ser Thr Pro Val Asp Gly Trp Glu Leu Asp Phe Thr Leu Pro
        290                 295                 300

Ala Gly His Thr Val Thr Ser Val Trp Asn Ala Leu Ile Ser Pro Ala
305                 310                 315                 320

Ser Gly Ala Val Thr Ala Arg Ser Thr Gly Ser Asn Gly Arg Ile Ala
                325                 330                 335

Ala Asn Gly Gly Thr Gln Ser Phe Gly Phe Gln Gly Thr Ser Ser Gly
            340                 345                 350

Ala Gly Phe Thr Ala Pro Ala Gly Ala Arg Leu Asn Gly Thr Ser Cys
        355                 360                 365

Thr Val Arg
    370
```

<210> SEQ ID NO 2
<211> LENGTH: 1116
<212> TYPE: DNA
<213> ORGANISM: Unknown
<220> FEATURE:
<223> OTHER INFORMATION: Nearest "neighbor" = Streptomycetes thermovebaceous

<400> SEQUENCE: 2

```
atgagatccc atcccgctc cgcgacgatg accgtcctcg tcgtcctggc ctcgctcggc      60
gcgctgctca ccgcagcggc tcccgcccag gcgaaccagc agatctgcga ccgctacggc    120
accaccacga tccaggaccg gtacgtggtg cagaacaacc gctggggcac cagcgccacc    180
cagtgcatca atgtgaccgg caacggtttc gagatcaccc aggccgacgg ttcggtgccg    240
accaacggcg ccccgaagtc ctatccctcg gtctacgacg gctgccacta cggcaactgc    300
gcgccccgca cgacgctgcc catgcggatc agctcgatcg gcagcgcgcc cagcagtgtc    360
tcctaccgct acaccggcaa cggcgtctac aacgccgcgt acgacatctg gctggacccg    420
acaccccgca ccaacggggt gaaccggacc gagatcatga tctggttcaa ccgggtcggc    480
ccggtccagc ccatcggttc gccggtcggc acggcccacg tcggcggccg cagctgggag    540
gtgtggaccg gcagcaacgg ttcgaacgac gtgatctcct tcctggcgcc ctccgcgatc    600
agcagctgga gcttcgacgt caaggacttc gtcgaccagg ccgtcagcca cggcctggcc    660
accccggact ggtacctcac cagcatccag gcgggcttcg agccgtggga gggcggcacc    720
ggtctggccg tgaactcgtt ctcctccgcg gtgaacgccg ggggcgggaa cggcggcact    780
ccggggacac cggcggcctg ccaggtctcc tacagcaccc acacctggcc cggcggcttc    840
accgtcgaca ccaccatcac caataccggc tccacacccg tcgacggctg ggaactggac    900
ttcaccctcc ccgccggtca cacggtcacc agcgtgtgga acgcgctgat cagccccgcc    960
tcgggcgcgg tcacggcacg cagcaccggc tccaacggcc ggatcgcggc caacggcggg   1020
acccagtcct tcggtttcca gggcacctcc agcggagcgg ggttcaccgc accggccggg   1080
gcccggctca acggcacctc ctgcacagtg agatga                            1116
```

<210> SEQ ID NO 3
<211> LENGTH: 463
<212> TYPE: DNA
<213> ORGANISM: Unknown
<220> FEATURE:
<223> OTHER INFORMATION: Nearest "neighbor" = Streptomycetes thermovebaceous

<400> SEQUENCE: 3

| | | | | | |
|---|---|---|---|---|---|
| gaacgctggc | ggcgtgctta | acacatgcaa | gtcgaacgat | gaagccgctt | cggtggtgga | 60 |
| ttagtggcga | acgggtgagt | aacacgtggg | caatctgccc | tgcactctgg | acaagcccg | 120 |
| ggaaactggg | tctaataccg | gatatgacac | acgaccgcat | ggtctgtgtg | tggaaagctc | 180 |
| cggcggtgca | ggatgagccc | gcggcctatc | agcttgttgg | tggggtaatg | gcctaccaag | 240 |
| gcgacgacgg | gtagccggcc | tgagagggcg | accggccaca | ctgggactga | gacacggccc | 300 |
| agactcctac | gggaggcagc | agtggggaat | attgcacaat | gggcgaaagc | ctgatgcagc | 360 |
| gacgccgcgt | gagggatgac | ggccttcggg | ttgtaaacct | ctttcagcag | ggaagaagct | 420 |
| ttcgggtgac | ggtactgcag | aagaagcacc | ggctaactac | gtg | | 463 |

<210> SEQ ID NO 4
<211> LENGTH: 1716
<212> TYPE: DNA
<213> ORGANISM: Unknown
<220> FEATURE:
<223> OTHER INFORMATION: Nearest "neighbor" = Streptomycetes
      thermovebaceous

<400> SEQUENCE: 4

| | | | | | |
|---|---|---|---|---|---|
| ctagagtcga | ccacgcaggc | cgccaggtag | tcgacgttga | tctcgcagcc | gagcccggcc | 60 |
| ggaccggcgg | cgctgagcgc | gaggccgacg | gcgggacggc | cggcaccggt | acgcggtggc | 120 |
| gggtcgagtt | cggtgagcag | cccaccggcg | atcaggtcgt | cgacgagcgc | ggagacggtg | 180 |
| gcccgggtga | gcccggtgac | ggcggcaact | cccgcgcggg | agagccgatc | tgtgctgttt | 240 |
| gccacggtat | gcagcaccag | cgcgagatta | tgggctcgca | cgctcgactg | tcggacgggg | 300 |
| gcactggaac | gagaagtcag | gcgagccgtc | acgcccttga | caatgccaca | tcctgagcaa | 360 |
| ataattcaac | cactaaacaa | atcaaccgcg | tttcccggag | gtaaccatgg | ctttgggag | 420 |
| cgctcccatc | gcgttgtgtc | cgcttcgcac | gaggaggaac | gctttgaaac | gccttttggc | 480 |
| cctgctcgcg | accggcgtgt | cgatcgtcgg | cctgactgcg | ctagccggcc | cccggcaca | 540 |
| ggccaaccag | cagatctgcg | accgctacgg | caccaccacg | atccaggacc | ggtacgtggt | 600 |
| gcagaacaac | cgctggggca | ccagcgccac | cagtgcatca | atgtgaccgg | caacggtttc | 660 |
| gagatcaccc | aggccgacgg | ttcggtgccg | accaacggcg | gccccgaagt | cctatccctc | 720 |
| ggtctacgac | ggctgccact | acggcaactg | cgcgccccgc | acgacgctgc | ccatgcggat | 780 |
| cagctcgatc | ggcagcgcgc | ccagcagtgt | ctcctaccgc | tacaccggca | acggcgtcta | 840 |
| caacgccgcg | tacgacatct | ggctggaccc | gacaccccgc | accaacgggg | tgaaccggac | 900 |
| cgagatcatg | atctggttca | accgggtcgg | cccggtccag | cccatcggtt | cgccggtcgg | 960 |
| cacggcccac | gtcggcggcc | gcagctggga | ggtgtggacc | ggcagcaacg | gttcgaacga | 1020 |
| cgtgatctcc | ttcctggcgc | cctccgcgat | cagcagctgg | agcttcgacg | tcaaggactt | 1080 |
| cgtcgaccaa | ggccgtcagc | cacggcctgg | ccaccccgga | ctggtacctc | accagcatcc | 1140 |
| aggcgggctt | cgagccgtgg | gagggcggca | ccggtctggc | cgtgaactcg | ttctcctccg | 1200 |
| cggtgaacgc | cggggcggg | aacggcggca | ctccggggac | accggcggcc | tgccaggtct | 1260 |
| cctacagcac | ccacacctgg | cccggcggct | tcaccgtcga | caccaccatc | accaataccg | 1320 |
| gctccacacc | cgtcgacggc | tgggaactgg | acttcacccct | cccgccggt | cacacggtca | 1380 |
| ccagcgcgtg | gaacgcgctg | atcagccccg | cctcgggcgc | ggtcacggca | cgcagcaccg | 1440 |

```
gttccaacgg ccggatcgcg gccaacggcg ggacccagtc cttcggtttc cagggcacct    1500
ccagcggaac ggggttcaac gcaccggccg ggggccggct caacggcacc tcctgcacag    1560
tgagatgaca atggggatcc gcgagcggat cggctgaccg gagcggggag gaggacgggc    1620
ggccggcgga aaagtccgcc ggtccgctga atcgctcccc gggcacggac gtggcagtat    1680
cagcgccatg tccggcatat cccagccctc cgcatg                              1716
```

<210> SEQ ID NO 5
<211> LENGTH: 386
<212> TYPE: PRT
<213> ORGANISM: Unknown
<220> FEATURE:
<223> OTHER INFORMATION: Nearest "neighbor" = Streptomycetes thermovebaceous

<400> SEQUENCE: 5

```
Met Gly Phe Gly Ser Ala Pro Ile Ala Leu Cys Pro Leu Arg Thr Arg
 1               5                  10                  15

Arg Asn Ala Leu Lys Arg Leu Leu Ala Leu Ala Thr Gly Val Ser
            20                  25                  30

Ile Val Gly Leu Thr Ala Leu Ala Gly Pro Pro Ala Gln Ala Asn Gln
        35                  40                  45

Gln Ile Cys Asp Arg Tyr Gly Thr Thr Ile Gln Asp Arg Tyr Val
    50                  55                  60

Val Gln Asn Asn Arg Trp Gly Thr Ser Ala Thr Gln Cys Ile Asn Val
65                  70                  75                  80

Thr Gly Asn Gly Phe Glu Ile Thr Gln Ala Asp Gly Ser Val Pro Thr
                85                  90                  95

Asn Gly Ala Pro Lys Ser Tyr Pro Ser Val Tyr Asp Gly Cys His Tyr
            100                 105                 110

Gly Asn Cys Ala Pro Arg Thr Thr Leu Pro Met Arg Ile Ser Ser Ile
        115                 120                 125

Gly Ser Ala Pro Ser Ser Val Ser Tyr Arg Tyr Thr Gly Asn Gly Val
    130                 135                 140

Tyr Asn Ala Ala Tyr Asp Ile Trp Leu Asp Pro Thr Pro Arg Thr Asn
145                 150                 155                 160

Gly Val Asn Arg Thr Glu Ile Met Ile Trp Phe Asn Arg Val Gly Pro
                165                 170                 175

Val Gln Pro Ile Gly Ser Pro Val Gly Thr Ala His Val Gly Gly Arg
            180                 185                 190

Ser Trp Glu Val Trp Thr Gly Ser Asn Gly Ser Asn Asp Val Ile Ser
        195                 200                 205

Phe Leu Ala Pro Ser Ala Ile Ser Ser Trp Ser Phe Asp Val Lys Asp
    210                 215                 220

Phe Val Asp Gln Ala Val Ser His Gly Leu Ala Thr Pro Asp Trp Tyr
225                 230                 235                 240

Leu Thr Ser Ile Gln Ala Gly Phe Glu Pro Trp Glu Gly Gly Thr Gly
                245                 250                 255

Leu Ala Val Asn Ser Phe Ser Ser Ala Val Asn Ala Gly Gly Gly Asn
            260                 265                 270

Gly Gly Thr Pro Gly Thr Pro Ala Ala Cys Gln Val Ser Tyr Ser Thr
        275                 280                 285

His Thr Trp Pro Gly Gly Phe Thr Val Asp Thr Ile Thr Asn Thr
    290                 295                 300

Gly Ser Thr Pro Val Asp Gly Trp Glu Leu Asp Phe Thr Leu Pro Ala
```

```
                         -continued
305                 310                 315                 320
Gly His Thr Val Thr Ser Ala Trp Asn Ala Leu Ile Ser Pro Ala Ser
            325                 330                 335

Gly Ala Val Thr Ala Arg Ser Thr Gly Ser Asn Gly Arg Ile Ala Ala
            340                 345                 350

Asn Gly Gly Thr Gln Ser Phe Gly Phe Gln Gly Thr Ser Ser Gly Thr
        355                 360                 365

Gly Phe Asn Ala Pro Ala Gly Gly Arg Leu Asn Gly Thr Ser Cys Thr
    370                 375                 380

Val Arg
385
```

CELLULASE PRODUCING ACTINOMYCETES, CELLULASE PRODUCED THEREFROM AND METHOD OF PRODUCING SAME

CROSS-REFERENCE TO RELATED APPLICATIONS

This application is a continuation-in-part of U.S. Application Ser. No. 09/104,308, filed Jun. 24, 1998, now U.S. Pat. No. 6,187,577 which is a continuation-in-part of Ser. No. 08/974,042, filed Nov. 19, 1997, now abandoned; both of which are incorporated herein by reference in their entirety.

FEDERALLY SPONSORED RESEARCH AND DEVELOPMENT

Not Applicable.

BACKGROUND OF THE INVENTION

Cellulases are enzymes that hydrolyze the β-D-glucosidic linkages in celluloses. Cellulolytic enzymes have been traditionally divided into three major classes: endoglucanases, exoglucanases or cellobiohydrolases and β-glucosidases (Knowles, J. et al., *TIBTECH* 5:255–261 (1987)). Cellulases are known to be produced by a large number of bacteria, yeasts and fungi.

Primary among the applications that have been developed for the use of cellulolytic enzymes are those involving degrading (wood) cellulose pulp into sugars for (bio)ethanol production, textile treatments like "stone washing" and "biopolishing," and in detergent compositions. Cellulases are also known to be useful in detergent compositions for removing dirt, i.e., cleaning. For example, Great Britain Application Nos. 2,075,028, 2,095,275 and 2,094,826 illustrate improved cleaning performance with detergents that have incorporated cellulase. Additionally, Great Britain Application No. 1,358,599 illustrates the use of cellulase in detergents to reduce the harsh feel of cotton-containing fabrics.

Another useful feature of cellulases in the treatment of textiles is their ability to recondition used fabrics by making their colors more vibrant. For example, repeated washing of cotton containing fabrics results in a greyish cast to the fabric. This is believed to be due to disrupted and disordered fibrils, sometimes called "pills," caused by mechanical action. This greyish cast is particularly noticeable on colored fabrics. As a consequence, the ability of cellulase to remove the disordered top layer of the fiber and thus improve the overall appearance of the fabric has been found to be of value.

Because detergents, being a primary application of cellulase, operate generally under alkaline conditions there is a strong demand for cellulases that exhibit high activity at pH 7–10. Well characterized fungal cellulases, such as those from *Humicola insolens* and *Trichoderma reesei,* perform adequately at neutral to low alkaline pH. A number of enzymes demonstrating cellulase activity at high alkaline pH have been isolated from Bacillus and other prokaryotes, see e.g., PCT Publication Nos. WO 96/34092 and WO 96/34108. Thus, both fungal and bacterial cellulases have been investigated thoroughly. However, a third group of cellulases, those isolated from Actinomycetes, have attracted only meager attention. Wilson, et al., *Critical Reviews in Biotechnology,* 12:45–63 (1992), have studied cellulases produced by *Thermomonospora fusca, Thermomonospora curvata* and *Microbispora bispora* and have shown that many of these cellulases exhibit broad pH profiles and good temperature stability. Similarly, Nakai, et al., *Agric. Biol. Chem.,* 51: 3061–3065 (1987) and Nakai, et al., *Gene,* 65:229–238 (1988) have demonstrated the alkalitolerant cellulase casA from Streptomyces strain KSM-9. This cellulase possesses an alkaline pH optimum and excellent temperature stability.

Despite knowledge in the art related to many cellulase compositions having desirable properties, including some examples from Actinomycetes, there is a continued need for new cellulases having a varying spectrum of characteristics useful as, for example, textile treatments, components of detergent compositions, pulp and paper treatments, animal feed supplements, processing aids for baking, and biomass converters. Applicants have discovered cellulases which possess such a complement of characteristics and which are useful in such known applications of cellulases.

SUMMARY OF THE INVENTION

An object of the present invention is to provide novel cellulase compositions producible by Actinomycetes, derivatives of such cellulases, methods of producing such cellulases and the use of such cellulases. The present invention further relates to the use of the novel cellulase in compositions recognized in the art as advantageously having cellulase added thereto, including, as an additive in a detergent composition, in the treatment of textiles such as cellulose-containing fabrics and fibers useful therefor, as an animal feed additive, as a processing aid in baking, in the treatment of pulp and paper and in the treatment of starch for the production of high fructose corn-syrup or ethanol.

It is a further object of the present invention to provide for a method of producing cellulase compositions derived from such novel Actinomycetes via heterologous expression from recombinant host cells.

It is yet a further object of the present invention to provide a DNA and amino acid sequence which facilitate commercial production of the novel cellulase compositions of the invention.

It is still a further object of the present invention to provide a novel cellulase having excellent properties for use in detergents, treating textiles, as a feed supplement and in pulp and paper manufacturing.

According to the present invention, a novel cellulase or a derivative is provided which is obtainable from an Actinomycete. Preferably, the cellulase of the invention comprises an amino acid sequence according to FIG. 1 (SEQ ID NO:1), a fragment, or a derivative thereof, having greater than 50% sequence identity, preferably greater than 70% sequence identity and more preferably greater than 90% sequence identity to an active portion thereto.

According to another embodiment, a composition is provided comprising DNA encoding the cellulases of the invention. Preferably, the DNA encodes an amino acid sequence and comprises the nucleotide sequence as shown in FIG. 2 (SEQ ID NO:2), a fragment, or a derivative thereof, having greater than 76% sequence identity, preferably greater than 80% sequence identity and more preferably greater than 90% sequence identity to a portion thereto, and cellulases produced thereby. The present invention further embodies DNA which hybridizes to a DNA probe taken from the DNA represented in FIG. 2 under the appropriate conditions, and cellulases produced thereby.

According to yet another embodiment of the invention, a method of transforming a suitable microorganism with DNA encoding a cellulase according to the invention is provided and a method of producing the cellulase according to the invention from that transformed microorganism.

In a preferred embodiment of the present invention, a full-length cellulase is derived from Actinomycetes and has a molecular weight of approximately 36 kD as measured on SDS-PAGE (referred to herein as the 36 kD cellulase). The full-length, approximately 36 kD, cellulase has a calculated isoelectric point of about 5.9 and a pH optimum on CMC (carboxy methyl cellulose) of about 8 at 40° C. and 7 at 60° C. The cellulase of the present invention shows higher activity at 60° C. than at 40° C. with broad activity ranges from at least pH 5 to pH 10.

In an especially preferred embodiment, a cellulase of this invention is a truncated form of the full-length cellulase described above. Its molecular weight is approximately 25 kD.

BRIEF DESCRIPTION OF THE DRAWINGS

FIG. 1 shows the deduced amino acid sequence of an approximately 36 kD cellulase according to the invention showing the leader sequence in bold. (SEQ ID NO:1).

FIG. 2 shows the DNA sequence encoding an approximately 36 kD cellulase according to the invention (SEQ.ID.NO:2).

FIG. 3 shows the pH/activity profile of an approximately 36 kD cellulase according to the invention at 40° C. and 60° C.

FIG. 4 shows the pHPLT vector.

FIG. 5 shows the pHP11AG8 vector.

FIG. 6 shows the 16s RNA sequence of the Actinomycete from which the cellulase of the invention may be obtained (SEQ.ID.NO:3).

FIG. 7 indicates the construction of pIJ488-101.

FIG. 8 shows the construction of pWGxGIT.

FIG. 9 showns the construction of pTZ18Rsti.

FIG. 10 shows the construction of pWGxsGIT.

FIG. 11 shows the construction of pIJ488sti.

FIG. 12 shows the construction of pSEGCi.

FIG. 13 shows the construction of pSEGCT.

FIG. 14 shows the construction of pSEGCT11AG8.

FIG. 15 provides the DNA sequence of the complete expression cassette consisting of the GI promoter, the celA signal sequence, cellulase 11AG8 and the GI terminator (SEQ ID NO:4) Also provided therein is the coding amino acid sequence of 11AG8 (SEQ ID NO:5).

FIG. 16 shows the construction of pSEACT11AG8.

FIG. 17 shows the construction of pSACT11AG8.

FIG. 18 compares the performance of the full length and the truncated cellulase of this invention. FIG. 18a indicates that in Wisk®, the depilling performance of the full length is equivalent to that of the truncated cellulase. FIG. 18b indicates that the peak load values are slightly lower and TSL greater in the truncated cellulase. FIG. 18c indicates that at an equal depilling rate, the truncated cellulase has a greater TSL than the full length cellulase.

FIG. 19 compares the performance of the full length and the truncated cellulase of this invention. FIG. 19a indicates that in Gessy Lever #1, the depilling performance of the truncated cellulase was better than that of the full length cellulase.

FIG. 19b indicates the peak load values were greater for the truncated enzyme than for the full length cellulase.

FIG. 20 compares the performance of the full length and the truncated cellulase of this invention in the presence of a bleaching agent. FIG. 20a indicates that, in the presence of perborate monohydrate and a bleach activator, the truncated enzyme's depilling ability decreased the least. FIG. 20b shows that the peak load values increased for the truncated cellulase in the presence of a bleaching agent.

FIG. 21 compares the performance of the full length and the truncated cellulase of this invention in the presence of protease. FIG. 21a indicates that protease had no effect on the depilling performance of the truncated enzyme. FIG. 21b shows that protease had no effect on the peak load values for the truncated cellulase.

DETAILED DESCRIPTION OF THE INVENTION

Definitions

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole.

The term "amino acid" includes reference to an amino acid that is incorporated into a protein, polypeptide, or peptide (collectively "polypeptide"). The amino acid can be a naturally occurring amino acid or, unless otherwise limited, can encompass known analogs of natural amino acids that function in a similar manner as naturally occurring amino acids. "Derivative" is intended to indicate a peptide or protein that is derived from a native protein by addition of one or more amino acids to either or both the C- and N-terminal end of the native protein, substitution of one or more amino acids at one or a number of different sites in the native amino acid sequence, deletion of one or more amino acids at either or both ends of the native protein or at one or more sites in the amino acid sequence, or insertion of one or more amino acids at one or more sites in the native amino acid sequence. The preparation of an enzyme derivative is preferably achieved by modifying the DNA sequence that encodes the native protein, transformation of that DNA sequence into a suitable host, and expression of the modified DNA sequence to form the derivative enzyme. Alternative means of preparing derivatives are well known in the art, and include, e.g., proteolytic cleavage of native proteins or their derivatives. The derivatives of the cellulases of this invention include peptides comprising altered amino acid sequences in comparison with a precursor enzyme amino acid sequence (e.g., a wild type or native state enzyme according to the present invention) that retain a characteristic enzymatic nature of the precursor enzyme but which have altered properties in some specific aspect. For example, an altered cellulase may have an increased pH optimum or increased temperature resistance but will retain its characteristic cellulolytic activity.

"Conservative substitutions" of a particular amino acid sequence refers to amino acid substitutions of those amino acids that are not critical for functional activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art.

The term "identical" in the context of two polypeptide or nucleic acid sequences refers to the residues in the two sequences that are the same when aligned for maximum correspondence, as measured using one of the following "sequence comparison algorithms." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wi.), or by visual inspection.

An example of an algorithm that is suitable for determining sequence similarity is the BLAST algorithm, which is described in Altschul, et al., *J Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a cellulase nucleic acid of this invention if the smallest sum probability in a comparison of the test nucleic acid to a cellulase nucleic acid is less than about 0.1, more preferably less than about 0.01, and most preferably less than about 0.001. Where the test nucleic acid encodes a cellulase polypeptide, it is considered similar to a specified cellulase nucleic acid if the comparison results in a smallest sum probability of less than about 0.5, and more preferably less than about 0.2.

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution.

As used herein, "polypeptide," "peptide" and "protein" are used interchangeably and include reference to a polymer of amino acid residues. The terms apply to amino acid polymers in which one or more amino acid residue is an artificial chemical analog of a corresponding naturally occurring amino acid, as well as to naturally occurring amino acid polymers. The terms also apply to polymers containing conservative amino acid substitutions such that the polypeptide remains functional.

As used herein, "recombinant" includes reference to a polypeptide produced using host cells that do not have, in their native state, an endogenous copy of the DNA able to express the polypeptide. The host cells produce the recombinant polypeptide because they have been genetically altered by the introduction of the appropriate isolated nucleic acid sequence. The term also includes reference to a host cell, or nucleic acid, or vector, that has been modified by the introduction of a heterologous nucleic acid or the alteration of a native nucleic acid to a form not native to that cell, or that the host cell is derived from a cell so modified. Thus, for example, recombinant host cells express genes that are not found within the native (non-recombinant) form of the cell, express mutants of genes that are found within the native form, or express native genes that are otherwise abnormally expressed, under expressed or not expressed at all.

"Host cell" means a cell which has the capacity to act as a host and expression vehicle for a recombinant DNA vector according to the invention. In a preferred embodiment according to the present invention, "host cell" means the cells of Bacillus. However, one of skill will realize that any appropriate host cell, e.g., bacterial, fungal, eukaryotic and plant cell may be used.

"DNA construct" or "DNA vector" means a nucleotide sequence which comprises one or more DNA fragments encoding any of the novel cellulases or cellulase derivatives described above. Included in "DNA vectors" are "expression vectors." Typical expression vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in prokaryotes, eukaryotes, or both, (e.g., shuttle vectors) and selection markers for both prokaryotic and eukaryotic systems. Vectors are suitable for replication and integration in prokaryotes, eukaryotes, or both. See, Giliman and Smith, *Gene* 8:81–97 (1979); Roberts et al., *Nature* 328:731–734 (1987); Berger and Kimmel, GUIDE To MOLECULAR CLONING TECHNIQUES, METHODS IN ENZYMOLOGY, VOL 152, Academic Press, Inc., San Diego, Calif. ("Berger"); Scheider, B., et al., *Protein Expr. Purif.* 6435:10 (1995); Sambrook et al. MOLECULAR CLONING—A LABORATORY MANUAL (2ND ED.) VOL. 1–3, Cold Springs Harbor Publishing (1989)

("Sambrook"); and CURRENT PROTOCOLS IN MOLECULAR BIOLOGY, Ausubel et al. (eds.), Current Protocols, a joint venture between Greene Publishing Associates, Inc. and John Wiley & Sons, Inc., (1997 Supplement) ("Ausubel").

Cloning and Expression of Full Length Cellulase

In one embodiment of this invention, the cellulases of this invention are obtained from natural sources, e.g., are not recombinantly produced. It is possible to obtain the cellulases by screening soda lake samples to isolate the appropriate cellulase-producing organism. That organism can then be grown up according to art recognized means for growing bacteria, such as Actinomycetes.

However, rather than isolating the correct cellulase producing strain, it is more efficient to utilize genetic engineering techniques. Thus, it is possible to transform a suitable host cell with the DNA provided herein and cultivate the resultant recombinant microorganism under conditions appropriate for host cell growth and cellulase expression.

As a first step, chromosomal DNA may be obtained from the donor Actinomycete strain by, for example, the method of Saito and Miura (Saito & Miura, *Biochim. Biophys. Acta.*,72:619 (1963)) or by a similar method. Restriction enzyme cleavage of the chromosomal DNA thus obtained provides DNA fragments containing the alkaline cellulase gene. For this purpose, any restriction enzyme may be used provided it does not cleave a desired region of said gene, for example the coding region of a gene or a coding region and a promoter of a gene. In the alternative, a restriction enzyme may be used which cleaves the gene, using however, a reduced enzyme concentration or incubation time to permit only partial digestion. A preferred restriction endonuclease is Sau3A. From the resulting digestion mixture, suitable fragments of about 4–10 kb may be isolated, inserted into a DNA vector, and used to transform a suitable host cell.

Genes encoding the cellulases of the present invention can be cloned using e.g., λ-phage (expression) vectors and *E. coli* host cells. (Alternatively PCR cloning using consensus primers designed on conserved domains may be used). After a first cloning step in *E. coli,* a cellulase gene according to the present invention can be transferred to a more preferred industrial expression host such as Bacillus or Streptomyces species, a filamentous fungus such as Aspergillus or Trichoderma, or a yeast such as Saccharomyces. Preferred are the bacterial species belonging to Bacillus or Streptomyces. Most preferred is Streptomyces. Also preferred is Trichoderma. However, it has been noticed that cellulases which have been fermented in Trichoderma increase the level of backstaining in used textile processing, e.g., stone washing. Without wishing to be limited by theory, it is believed that addition of protease to the fermentation media reduces backstaining to acceptable levels. Thus, Trichoderma could also provide an acceptable host cell for cellulases to be used in textile processing. High level expression and secretion obtainable in these host organisms allows accumulation of the cellulase in the fermentation medium from which it can subsequently be recovered.

The cellulase may be recovered from the fermentation medium by conventional procedures including separating the cells from the medium by centrifugation or filtration, or if necessary, disrupting the cells and removing the supernatant from the cellular fragments and debris. Typically, after clarification, the proteinaceous components of the supernatant or filtrate are precipitated by means of a salt, e.g., ammonium sulfate. The precipitated proteins are then solubilized and purified by a variety of chromatographic procedures, e.g., ion exchange chromatography, affinity chromatography or another similarly art-recognized procedure. For the production of a cellulase according to the invention, it is preferred to cultivate the host cells under alkaline conditions using media containing a cellulose-based energy source.

It is preferred that purification of the cellulases of this invention be monitored by functional activity. A preferred functional assay monitors the kinetics of hydrolysis of NPC (nitrophenyl cellobioside) by cellulase. The procedure is as follows:

In duplicate or triplicate wells of a 96-well microtiter plate, add 20 μL of sample or standard. The standards can be previously obtained and well-characterized cellulase samples, or commercially supplied cellulases. Add 100 μL of assay solution. The assay solution is 1 part concentrated stock and 5 parts phosphate buffer. The concentrated stock consists of 25 mg/mL NPC (Sigma N4764) in 100 mM sodium phosphate, pH 8.0. The same phosphate buffer can be used to dilute the assay solution. As soon as the NPC substrate has been added to the samples or standards, insert the plate in a 30° C. pre-heated microtiter plate reader. Readings at 1410 nm should be taken at 1 minute intervals for 6 minutes.

A standard curve can be generated from the standards. The y-axis of the curve is the Vmax and the X-axis is the concentration of the cellulase in the standard. If the Vmax of the samples falls outside of the standard curve created by the standards, the samples should be diluted and the assay repeated.

In one embodiment of this invention, the expression host cell comprises a Bacillus spp., more preferably *Bacillus licheniformis* or *Bacillus subtilis*. However, in a preferred embodiment, the host expression cells comprise a Streptomyces spp, more preferably *Streptomyces lividens*. A preferred general transformation and expression protocol for protease deleted Bacillus strains is provided in Ferrari, et al., U.S. Pat. No. 5,264,366, incorporated herein by reference. Transformation and expression in Aspergillus is described in, for example, Berka, et al., U.S. Pat. No. 5,364,770, incorporated herein by reference. Transformation and expression in Streptomyces can be found in Hopwood, et al., GENETIC MANIPULATION OF STREPTOMYCES: A LABORATORY MANUAL, Innis (1985), which is herein incorporated by reference in its entirety.

It was found that transformation of the DNA sequences of this invention into Bacillus was ineffective in terms of resulting expression. Thus, it is preferred, when transforming Bacillus spp., to utilize the aprE promoter in combination with known Bacillus-derived signal and other regulatory sequences. When the transformation host cell is Aspergillus the preferred promoter is glaA. With Streptomyces, the preferred promoter is the Glucose Isomerase (GI) promoter of *Actinoplanes missouriensis.*

In addition to a full-length cellulase and DNA encoding it, this invention also encompasses truncated cellulases, and derivatives of cellulases and the DNA encoding them. Typically, cellulases comprise two active domains: a catalytically active domain and a cellulose binding domain. The truncated cellulases of this invention comprise the catalytically active portion of a full-length cellulase of this invention.

In one embodiment, the truncated cellulase is produced by the cleavage of a full-length cellulase. The full-length cellulase can either be isolated from its natural host, e.g., Actinomyctes or from a recombinant host cell. Without wishing to be limited by theory, it is believed that during the fermentation process of recombinant host cells, a protease truncates the cellulases of this invention. In particular, it is believed an endoprotease that cleaves after proline residues truncates the cellulases. Thus, it is envisioned that, in the case of non-recombinant cellulases or recombinant cellulases that are not truncated during the fermentation process, such a protease can be added to the full length cellulases of this invention to produce the truncated forms.

After cleavage, it may be necessary to separate the truncated cellulase of this invention from the now-separate cellulase binding domain. This separation can be done on the basis of size by e.g., preparative electrophoresis, gel filtration or size exclusion chromotography, and ultrafiltration. Other possible methods will be apparent to those of skill in the art and may include, ion exchange chromatography, hydrophobic interaction chromatography and affinity chromatography, sedimentation equilibrium, etc.

Alternatively, a truncated cellulase can be recombinantly made. In this aspect, a DNA sequence is prepared that comprises only the coding region for the catalytically active portion of a full-length cellulase. In preferred embodiments, the DNA encoding the 230 or 233 amino acids of the catalytically active domain is prepared. The DNA sequence can be prepared either through synthetic means or by restriction enzyme digestion of a full-length coding sequence. If a restriction enzyme is used, depending on the enzyme, it may be necessary to blunt end any protruding single strands of DNA. Such blunt ending can be done by filling in the other, non-protruding strand, or by trimming the protruding strand. Techniques for both of these methods are well known to those of skill. One of skill will also know that a stop codon should be added after the desired coding region has terminated. Techniques for adding codons to the 3' end of a coding region are well known and can be found in, for example, Ausubel or Sambrook.

Synthesis of DNA sequences is well known in the art and can be found in, for example, Beaucage & Caruthers, *Tetrahedron Letts.* 22(20):1859–1862 (1981), e.g., using an automated synthesizer, e.g., as described in Needham-VanDevanter, et al., *Nucl Acids Res.* 12:6159–6168 (1984). DNA sequences can also be custom made and ordered from a variety of commercial sources known to persons of skill, for example, Promega (Madison, Wis.). Purification of DNA sequences, where necessary, is typically performed by either native acrylamide gel electrophoresis or by anion-exchange HPLC as described in Pearson & Regnier, *J. Chrom.* 255:137–149 (1983). The sequence of the synthetic oligonucleotides can be verified using the chemical degradation method of Maxam & Gilbert, *Methods in Enzymology* 65:499–560 (1980).

In an alternative method, it may be preferable to keep the coding region of the full-length cellulase gene intact but to introduce a stop codon at the desired truncation point. There are many ways of generating alterations in a given nucleic acid sequence to, e.g., insert a stop codon which can truncate a polypeptide. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman & Smith, *Gene* 8:81–97 (1979); Roberts, et al., *Nature* 328:731–734 (1987); Sambrook; and Ausubel.

In addition to truncated cellulases, this invention encompasses other derivatives of full-length and truncated cellulases. Such derivatives comprise, e.g., amino acid substitutions, substitution of non-natural amino acids, substitution or addition of D-amino acids, and conjugation to another moiety. With the exception of amino acid substitutions, which can be accomplished in a similar manner to that described above for the insertion of a stop codon, the substitution of non-natural amino acids and conjugation to other moieties should be done chemically. Techniques for chemical modification of proteins are well known in the art and can be found in, for example, CHEMISTRY AND BIOCHEMISTRY OF AMINO ACIDS, PEPTIDES, AND PROTEINS, B. Weinstein, (ed.), Marcel Dekker, New York, p. 267 (1983).

Identification of the Cellulases of this Invention

Thus, the present invention encompasses a cellulase that has an amino acid sequence according to that in FIG. 1 (SEQ ID NO:1), a fragment, or a derivative thereof having greater than 50% sequence identity, preferably greater than 70% sequence identity, and most preferably greater than 90% sequence identity thereto. Similarly, the present invention further encompasses a DNA according to FIG. 2 (SEQ. ID NO:2), a fragment, or a derivative thereof having greater than 76% sequence identity, preferably greater than 80% sequence identity and most preferably greater than 90% sequence identity thereto.

In addition to full-length cellulases, this invention provides for truncated forms of full-length cellulases. Preferably, the truncated cellulase has an amino acid sequence as represented by SEQ ID NO:1 from amino acid position 31 to amino acid at position 261 or 264 or is a derivative of such a sequence having greater than 50% sequence identity, preferably greater than 70% sequence identity, and most preferably greater than 90% sequence identity. Similarly, the present invention further encompasses a DNA that encodes a truncated cellulase or a derivative thereof wherein the sequence corresponds to a DNA sequence as shown in FIG. 2 (SEQ. ID NO:2) or a derivative thereof having greater than 76% sequence identity, preferably greater than 80% sequence identity and most preferably greater than 90% sequence identity thereto. Preferably the DNA sequence comprises nucleotides starting at position 93 and extend to position 783 or 792 of SEQ ID NO:2, inclusive.

In a preferred embodiment, hybridization is used to analyze whether a given DNA fragment or gene corresponds to a cellulase DNA sequence described herein and thus falls within the scope of the present invention. The hybridization assay is essentially as follows: Genomic DNA from a particular target source is fragmented by digestion with an appropriate restriction enzyme, e.g., EcoRI, Hind III, Bam HI, Cla I, Kpn I, Mlu I, Spe I, Bgl II, Nco I, Xba I, Xho I and Xma I (supplied by new England Biolabs, Inc., Beverly, Mass. and Boehringer Mannheim) according to the manufacturer's instructions. The samples are then electrophoresed through an agarose gel (for example, 0.8% agarose) so that separation of DNA fragments can be visualized by size. DNA fragments are typically visualized by ethidium bromide staining. The gel may be briefly rinsed in distilled $H_2O$ and subsequently depurinated in an appropriate solution (such as, for example, 0.25M HCl) with gentle shaking followed by denaturation for 30 minutes (in, for example, 0.4 M NaOH) with gentle shaking. A renaturation step may be included, in which the gel is placed in 1.5 M NaCl, I MTris, pH 7.0 with gentle shaking for 30 minutes. The DNA should then be transferred onto an appropriate positively charged membrane, for example, Maximum Strength Nytran Plus membrane (Schleicher & Schuell, Keene, N. H.), using a transfer solution (such as, for example, 6×SSC (900 mM NaCl, 90 mM trisodium citrate). Once the transfer is complete, generally after about 2 hours, the membrane is rinsed in e.g., 2×SSC (2×SSC=300 mM NaCl, 30 mM trisodium citrate) and air dried at room temperature. The membrane should then be prehybridized (for approximately 2 hours or more) in a suitable prehybridization solution (such as, for example, an aqueous solution containing per 100 mL: 20–50 mL formamide, 25 mL of 20×SSPE (1×SSPE=0.18 M NaCl, 1 mM EDTA, 10 mM $NaH_2PO_4$, pH 7.7), 2.5 mL of 20% SDS, and 1 mL of 10 mg/mL sheared herring sperm DNA). As would be known to one of skill in the art, the amount of formamide in the prehybridization solution may be varied depending on the nature of the reaction obtained according to routine methods. Thus, a lower amount of formamide may result in more complete hybridization in terms of identifying hybridizing molecules than the same procedure using a larger amount of formamide. On the other hand, a strong hybridization band may be more easily visually identified by using more formamide.

A DNA probe generally between 100 and 1000 bases in length taken from the sequence in FIG. 2 should be isolated by electrophoresis in an agarose gel, the fragment excised from the gel, and recovered from the excised agarose. For a more detailed procedure, see Sambrook. This purified fragment of DNA is then labeled (using, for example, the Megaprime labeling system according to the instructions of the manufacturer) to incorporate $p^{32}$ in the DNA. The labeled probe is denatured by heating to 95° C. for 5 minutes and immediately added to the membrane and prehybridization solution. The hybridization reaction should proceed for an appropriate time and under appropriate conditions, for example, for 18 hours at 37° C. with gentle shaking or rotating. The membrane is rinsed (for example, in 2×SSC/0.3% SDS) and then washed in an appropriate wash solution with gentle agitation. The stringency desired will be a reflection of the conditions under which the membrane (filter) is washed.

Specifically, the stringency of a given reaction (i.e., the degree of homology necessary for successful hybridization) will depend on the washing conditions to which the filter is subjected after hybridization. "Low-stringency" conditions as defined herein will comprise washing a filter with a solution of 0.2×SSC/0.1% SDS at 20° C. for 15 minutes. "High-stringency" conditions comprise a further washing step comprising washing the filter a second time with a solution of 0.2×SSC/0.1% SDS at 37° C. for 30 minutes.

After washing, the membrane is dried and the bound probe detected. If $^{32}P$ or another radioisotope is used as the labeling agent, the bound probe can be detected by autoradiography. Other techniques for the visualization of other probes are well-known to those of skill. The detection of a bound probe indicates a nucleic acid sequence has the desired homology, and therefore identity to SEQ ID NO:2, and is encompassed within this invention.

The cellulase proteins and derivatives of this invention can be characterized either physicochemically or functionally, and preferably both. Physicochemical characterization takes advantages of well known techniques such as SDS electrophoresis, gel filtration, amino acid composition, mass spectroscopy and sedimentation to determine the molecular weight of a protein, isoelectric focusing to determine the pI of a protein, amino acid sequencing to determine the amino acid sequence of a protein, crystallography studies to determine the tertiary structure of a protein, and antibody binding to determine antigenic epitopes present in a protein.

Functional characteristics are determined by techniques well known to the practitioner in the cellulase field and include, but are not limited to, hydrolysis of crystalline carboxy methylcellulose (CMC). This preferred technique for functional characterization is described in greater detail in Example 5, below.

Using some of the techniques listed above, the full-length cellulases of this invention were found to have a molecular weight of approximately 30 to 40 kD, preferably 34 to about 38 kD, and most preferably 36 kD as measured on SDS-PAGE. The full-length cellulases were found to have a calculated isoelectric point of about 4 to about 5, preferably 4.5, and a pH optimum on CMC of about 5 to about 10, depending on the temperature. The pH optimum was found to be 8 at 40° C. and 7 at 60° C. The truncated cellulases of this invention were found to have a molecular weight of between 20 and 30 kD, preferably between about 23 and 26 kD and most preferably between 24 and 25 kD.

Uses of the Cellulases of this Invention

Treatment of textiles according to the present invention contemplates textile processing or cleaning with a composition comprising a cellulase of this invention. Such treating includes, but is not limited to, stonewashing, modifying the texture, feel and/or appearance of cellulose-containing fabrics or other techniques used during manufacturing or cleaning/reconditioning of cellulose-containing fabrics. Additionally, treating within the context of this invention contemplates the removal of "immature" or "dead" cotton from cellulosic fabric or fibers. Immature cotton is significantly more amorphous than mature cotton and because of, for example, uneven dyeing. The composition contemplated in the present invention further includes a cellulase component for use in washing a soiled manufactured cellulose-containing fabric. For example, a cellulase of this invention may be used in a detergent composition for washing laundry. Detergent compositions useful in accordance with the present invention include special formulations such as prewash, pre-soak and home-use color restoration compositions. Such treating compositions, as described herein, may be in the form of a concentrate which requires dilution or in the form of a dilute solution or form which can be applied directly to the cellulose-containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulases are known to increase the value of animal feed, improve the drainability of wood pulp, enhance food products and reduce fiber in grain during the grain wet milling process or dry milling process.

Treating according to the instant invention comprises preparing an aqueous solution which contains an effective amount of a cellulase or a combination of cellulases together with other optional ingredients including, for example, a buffer, a surfactant, and/or a scouring agent. An effective amount of a cellulase enzyme composition is a concentration of cellulase enzyme sufficient for its intended purpose. Thus, for example, an "effective amount" of cellulase in a stone-washing composition according to the present invention is that amount which will provide the desired effect, e.g., to produce a worn and faded look in seams and on fabric panels. Similarly, an "effective amount" of cellulase in a composition intended for improving the feel and/or appearance of a cellulose-containing fabric is the amount that produces measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose-containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity. The pH at which the cellulase exhibits activity depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity. The determination of the optimal pH range of the cellulases of the invention can be ascertained according to well known techniques. Suitable buffers at pH within the activity range of the cellulase are also well known to those skilled in the art in the field.

In addition to cellulase and a buffer, the treating composition may optionally contain a surfactant. Suitable surfactants include any surfactant compatible with the cellulase being utilized and the fabric including, for example, anionic, non-ionic and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include, but are not limited to, alkali metal ions such as sodium and potassium; alkaline earth metal ions such as calcium and magnesium; ammonium ion; and alkanolamines having 1 to 3 alkanol groups of carbon number 2 or 3. Ampholytic surfactants include, e.g., quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates permit facile formulation of the cellulase solutions as well as permit feasible transportation of the composition to the location where it will be used. The treating concentrate can be in any art-recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the cellulase composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, i.e., improving the feel and/or appearance of a fabric. The cellulose-containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose-containing fabric. When the stonewashing composition is in a solid form, for example a pre-wash gel or solid stick, the stonewashing composition may be contacted by directly applying the composition to the fabric or to the wash liquor.

The cellulose-containing fabric is incubated with the stonewashing solution under conditions effective to allow the enzymatic action to confer a stonewashed appearance to the cellulose-containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the cellulase enzyme to react efficiently with cellulose-containing fabric, in this case to produce the stonewashed effect. It is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., and these conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all effect the optimal reaction time. Generally, reaction times are from about 5 minutes to about 5 hours, and preferably from about 10 minutes to about 3 hours and, more preferably, from about 20 minutes to about I hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose-containing fabrics, for example, depilling, softening, anti-pilling, surface fiber removal, anti-graying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase protecting agent. The granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, non-ionic and ampholytic surfactants well known for their use in detergent compositions.

Suitable anionic surfactants for use in the detergent composition of this invention include linear or branched alkyl-benzenesulfonates; alkyl or alkenyl ether sulfates having linear or branched alkyl groups or alkenyl groups; alkyl or alkenyl sulfates; olefinsulfonates; and alkanesul-fonates. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyal-kylene ethers, as well as higher fatty acid alkanolamides or alkylene oxide adduct thereof, fatty acid glycerine monoesters, and the like. Suitable surfactants for use in this invention are disclosed in British Patent Application No. 2 094 826 A, the disclosure of which is incorporated herein by reference. Mixtures of such surfactants can also be used. The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. In addition to the cellulase composition and the surfactant(s), the detergent compositions of this invention can optionally contain one or more of the following components:

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic Surfactants and Long-Chain Fatty Acid Salts

Such cationic surfactants and long-chain fatty acid salts include saturated or unsaturated fatty acid salts, alkyl or alkenyl ether carboxylic acid salts, α-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent sequestering agents

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or inorganic electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

The solubilizers include, for example, lower alcohols such as ethanol, benzenesulfonate salts, lower alkylbenzenesulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or a nonhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose-containing fabric, for example soiled fabrics, in industrial and household uses at temperatures, reaction times and liquor ratios conventionally employed in these environments.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

It is contemplated that compositions comprising cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Example 1
Isolation of Cellulase Producing Micro-organisms from Alkaline Soil and Water Samples Alkaline mud samples were suspended in 5 ml 4% (w/v) NaCl, 1% (w/v) $Na_2CO_3$, and shaken vigorously. Serial dilutions in the same solution were plated out on Soil Extract Agar, pH 10 containing rifampicine 50 µg/mL.

Soil Extract Agar was prepared as follows: 1 kg of garden soil was suspended in 1 liter of demineralized (demi) water. The suspension was autoclaved for 20 minutes at 120° C. The suspension was filtered over a glass fiber filter (Whatman, GF/A) and the solids washed twice with demi water (1×200 ml, 1×100 ml). The filtrate is made up to 1 liter with water. An equal volume of sterilized filtrate was mixed with a sterile solution of 8% (w/v) NaCl, 2% (w/v) $Na_2CO_3$ with 2% (w/v) agar added for solidification.

The plates were incubated at 30° C. for several weeks in a closed box to prevent evaporation. The plates were examined periodically under the stereo-microscope and microcolonies were transferred to Alkaline Agar containing 0.3% (w/v) carboxymethylcellulose (CMC). Duplicate cultures were used to detect cellulase activity. The duplicate plates were flooded with 0.1% (w/v) Congo Red for 15 minutes and destained with 1M NaCl for 30 minutes. The strains that exhibited a clearing zone around the colonies were selected as potential cellulase producing micro-organisms.

Strains that showed clearing zones were fermented in 25 mL as described in PCT Publication No. WO 96/34108 after which CMC was added.

Using the method described above, the strain that produced a cellulase according to the invention was isolated and further characterized as filamentous bacteria. Based on appearance and partial 16s rRNA gene sequence analysis (Example 4), the microorganism was classified as a species of Streptomyces.

A morphological examination of the cellulase producing strain was made. When grown on Soil Extract Agar at pH 10; the initially small round glistening transparent colony developed after a few days a white to gray-white aerial mycelium. On Alkaline Agar the strain formed a dry leathery, cream colored, opaque colony producing aerial mycelium on maturity. Under the microscope, the strain exhibited extensively branched pseudo-mycelium which fragmented into irregular rods, isolated spores and spores in chains.

Example 2
Isolation of DNA, Transformation and Expression of Cellulase

An alkaliphilic Actinomycete strain isolated according to Example 1 was chosen as a donor strain for expression cloning in *E. coli* Chromosomal DNA was isolated according to the method described by Saito & Miura, *Biochim. Biophys. Acta.*, 72:619–629 (1963).

The isolated chromosomal DNA was partially digested by the restriction enzyme Sau3A using serial diluted enzyme solutions for one hour at 37° C. using React Buffers (Gibco BRL Life Technologies, Gaithersburg, Md., USA) under conditions recommended by the supplier. The digested DNA was fractionated by agarose gel electrophoresis and suitable fractions (2–6 kb) were isolated from the gel using QIAquick Gel Extraction Kit according to the protocol described by the supplier (QIAGEN Inc., Chatsworth, Calif., USA).

Genomic gene libraries of the alkalitolerant Actinomycete strains were constructed in a pUC19-derived plasmid (Yanisch-Perron, C. et al., *Gene* 33:103 (1985)). Recombinant clones were screened by agar diffusion as described by Wood, et at., *Meth. Enzym.*, 160:59–74 (1988). Strains that showed clearing zones around the colonies were isolated. Plasmid DNA of the cellulase producing recombinant was isolated using a QIAprep Plasmid Kit according to the protocol described by the supplier (QIAGEN Inc.). The nucleotide sequence of a 3.5 kb fragment was determined from both ends until a sequence bearing resemblance to known conserved cellulase sequences was identified by a FASTA search against the public databases. Upon determination of conserved sequences, the remainder of the gene was sequenced.

The isolated gene contained 1173 base pairs coding for a precursor protein having 371 amino acids including a signal sequence of 27 amino acids. The mature protein comprised 344 amino acids for a deduced molecular weight of 35,766 and a calculated pI of 5.9. The nucleotide sequence of the gene (SEQ. ID. NO:2) coding for the cellulase and the deduced amino acid sequence (SEQ ID NO:1) of the mature cellulase are illustrated in FIGS. 1 and 2.

The DNA fragment of the cellulase gene coding for the structural gene prepared as described above was cloned in the vector pHPLT (see FIG. 4). This vector already contained the promoter and signal sequence of the thermostable amylase gene of *Bacillus licheniformis* and had been found to deliver high expression in Bacillus (see FIG. 5). Transformation of competent Bacillus host cells was performed with resulting recombinant cellulase producing Bacillus clones isolated and grown under suitable conditions for producing the cloned cellulase.

The gene encoding the amino acid sequence of the 36 kD cellulase was analyzed by comparison with the accessible sequence data in various libraries (GenBank, Swiss-Prot, EMBL and PIR) was performed to determine the close phylogenetic neighbors. The highest amount of homology found was to endoglucanase I from *Aspergillus aculeatus*, exocellobiohydrolase from *Cellulomonas fimi* and endoglucanase C from *Clostridium cellulovorans*. The approximately 36 kD cellulase was shown to be 35.1% identical in sequence to endoglucanase I from *Aspergillus aculeatus* in a 242 residue overlap, 48.2% identical in sequence to exocellobiohydrolase from *Cellulomonas fimi* in a 112 residue overlap and 44.7% identical to endoglucanase C from *Clostridium cellulovorans* in a 114 amino acid overlap using the TFASTA program as described by Pearson & Lipman, *Proc. Nat. Acad. Sci.*, 85:2444–2448 (1988). The TFASTA Data Searching Program is commercially available in the Sequence Analysis Software Package Version 6.0 (Genetic Computer Group, Univ. Wisconsin Biotechnology Center, Madison, Wis. 53705). A comparison of the DNA sequences encoding the 36 kD cellulase with DNA sequences in the public databases indicate that the closest homology was to the gene encoding eg1S from *Streptomyces rochei* (75.8% identity in an 823 base pair overlap) and to the gene encoding celB from *Streptomyces lividans* (74.9% identity in a 765 base pair overlap).

Example 3
Purification of Cellulase

The cellulase producing *Bacillus licheniformis* clones from Example 2 were grown in a complex medium comprising Trypton Soya Broth (Oxoid CM 129) 3%, 20 μg/mL neomycin. Purification of the recombinant cellulase may be accomplished as follows: Fermentation broth is separated from the culture liquid by centrifugation (8000 rpm). The cellulase in the supernatant is precipitated with ammonium sulphate (65% saturation). The precipitate is dissolved in 25 mM phosphate buffer pH 7+5 mM EDTA until a conductivity of 7 mS/cm was achieved. This solution is applied to a Q-Sepharose FF (diameter 5 cm, length 10 cm) Anion Exchange column, after which the column is washed with 25 mM phosphate buffer pH 7+5 mM EDTA until an absorbency of 0.2 AU. A gradient of 0 to 0.5M NaCl in 25 mM phosphate pH7 is applied to the column in 80 minutes followed by a gradient from 0.5 to 1M NaCl in 10 minutes. Elution may be performed in the first gradient. After elution the column is cleaned (upflow) with 1M NaOH and equilibrated again with 25 mM phosphate pH 7+5 mM EDTA.

Example 4
Characterization of 16S rDNA from Cellulase Producing Actinomycete

The nucleotide sequence of the first 400 bps of the 16S-rDNA sequence of the cellulase-producing organism isolated in Example 1 was obtained and is provided in FIG. 6 (SEQ.ID.NO:3). This sequence was analyzed with the FASTA sequence analysis software package to provide a comparison with the sequences in public databases. The analysis results illustrated that the nearest neighbor was *Streptomyces thermoveolaceous* which had a 16S rDNA identity of 95.5% in an overlap of 465 base pairs. The percentage of identity of the partial 16S rDNA fraction of the strains is a strong indication that the strain represents an unknown species of Actinomycetes. Based on an analysis of the obtained 16S rRNA sequence (in combination with the appearance, Example 1), the microorganism was classified as a species of Streptomyces.

Example 5
Properties of the Cellulase According to the Invention

To determine the pH/temperature profile of the approximately 36 kD cellulase of this invention, the activity of the cellulase was measured on CMC at various pH and temperature values. The assay was a colorimetric method for the determination of (total) cellulase activity, utilizing Carboxy Methyl Cellulose (CMC) as substrate. Detection of cellulase as based on the release of reducing sugars from cellulose by cellulase. The free sugars react with "PAHBAH" at high pH and temperature. This reaction product was measured with a spectrophotometer. The activity was determined using a calibration curve of glucose.

Chemicals:
 CMC, low viscosity (Sigma C-5678, batch # 23HO244)
 p-Hydroxybenzoic acidhydrazide ("PAHBAH",Sigma H-9882)
 D-glucose monohydrate (Boom 8342)
 $NaH_2PO_4$*1 aq (Merck 6346)
 $H_3PO_4$ (85%; Merck 573)
 Citric acid*1 aq (Merck 244)
 4N NaOH
 0.5N HCl Incubation buffer A (0.01M phosphate)
 1.38 g $NaH_2PO_4$*1 aq was dissolved in 800 mL of demi water. The pH was adjusted to 7 with 4N NaOH and the mixture was filled up to 1000 mL with demi water. Finally the pH was checked and adjusted if necessary. This buffer was used for dissolving and diluting the enzyme samples.

Incubation buffer B (0.1M citrate+0.1M phosphate)
 23.06 g $H_3PO_4$ was dissolved in demi water to a final volume of 200 mL (=1M). 42 g citric acid was dissolved in demi water to a final volume of 200 mL (=1M). 20 mL citric acid solution was added to 20 mL phosphoric acid, and then made to 150 mL with demi water. The pH (to range from 4 to 10) was adjusted with 4N NaOH and the final volume made to 200 mL with demi water. This buffer was used for diluting the substrate preparation.

Incubation Buffer C (0.05M Citrate+0.05M Phosphate):
 Incubation buffer B was diluted 1:1 with demi water. The pH was checked and corrected if necessary. This solution was used for the glucose calibration curve.

Substrate Preparation (1%):
 Under strong stirring, 1 g of CMC was slowly added to 100 mL of demi water. Vigorous stirring was continued for at least one hour followed by a treatment with an ultraturrax for 30 seconds.

Enzyme Solution
 The enzyme sample was dissolved and diluted in Incubation buffer A to an activity of about 0.05 U/mL (50% on the glucose calibration curve).

Color Reagent (5%)
 5 g PAHBAH was dissolved in 80 mL of 0.5N HCl, after which the solution was made to 100 mL with 0.5N HCl. Prior to use, one part of the PAHBAH solution was diluted with four parts of 0.5N NaOH.

Calibration Curve
 Stock solution #1: 1000 mg glucose was dissolved in 100 mL demi water (10 mg/ml).
 Stock solution #2: 0.5 mL stock solution #1 was diluted with 9.5 mL Incubation buffer C of the pH concerned (0.5 mg/ml).

The following titration scheme was used:

| μMol glucose/0.1 mL | stock solution #2 | incubation buffer C |
|---|---|---|
| 0 | 0 μL | 1000 μL |
| 0.05 | 200 μL | 800 μL |
| 0.1 | 400 μL | 600 μL |
| 0.15 | 600 μL | 400 μL |
| 0.2 | 800 μL | 200 μL |
| 0.25 | 1000 μL | 0 μL |

Assay Procedure
(1) test tubes of the glucose standards, controls, samples and blanks were filled with 0.5 mL of substrate (1%) and 0.5 mL Incubation buffer B of desired pH and placed in a waterbath at the desired temperature;

(2) the solutions were incubated for 10 minutes;
(3) 15 second intervals 100 μL glucose standard, control or sample at each pH was added to tubes with substrate;
(4) the solutions were vortexed for 3 seconds and placed back in the waterbath;
(5) each sample was incubated for 30 minutes;
(6) the enzyme reaction was stopped by adding 3 mL of the PAHBAH reagent;
(7) the resulting solutions were vortexed for 3 seconds and placed in a rack outside the waterbath;
(8) when all of the reactions had been stopped, 100 μL of sample was added to blank tubes and vortexed 3 seconds;
(9) the samples were placed for 15 minutes in a boiling water bath;
(10) the resulting samples were cooled down in cold tap water for 5 to 10 minutes and then revortexed for 3 seconds;
(11) the absorbance of the mixture was measured at 410 nm with water as a reference.

The results are shown in FIG. 3. As shown in FIG. 3, the pH optimum of the 36 kD cellulase was observed to be about 8 at 40° C. and 7 at 60° C.

Example 6
Cellulase Production in *Streptomyces lividans*

This example describes the construction of a plasmid comprising a nucleic acid encoding a cellulase of this invention and used to transform *Streptomyces lividans*. The final plasmid vector is referred to as pSEGCT.

The construction of pSEGCT made use of two other plasmids, pIJ486, described in Ward, et al., *Mol. Gen. Genet.* 203:468–478 (1986) and pIJ488. Plasmid pIJ488 is pUC18 (Yanisch-Perron, et al., *Gene* 33:103–119 (1985) containing, in its KpnI site, a 1.5 kb ermE fragment from *Saccharopolyspora erythrea* encoding erythromycin resistance. The nucleotide sequence of this fragment has been determined (Uchiyama & Weisblum, *Gene* 38:103–110 (1985) and Bibb, et al., *Gene* 38:215–226 (1985).

Both plasmids were originally derived from the natural Streptomyces plasmid pIJ101 (D. A. Hopwood, et al., *J. Gen. Microbiol.* 129:2257–2260 (1983). pIJ101 contains the tsr gene, encoding resistance to thiostrepton, from *Streptomyces azureus*. However, only the pIJ101 replication origin and replicase gene are still present in the pIJ486 and the pIJ488 plasmids.

Plasmid pIJ488-101 was constructed by ligating the large PstI fragment of pIJ486, containing the pIJ 101 replication origin and the thiostrepton resistance gene, with PstI digested pIJ488, yielding plasmid pIJ488-101 (see FIG. 7).

To introduce a suitable promoter, a plasmid was constructed from plasmid pIJ488-101 described above. The Glucose Isomerase gene of *Actinoplanes missouriensis* was introduced into plasmid pIJ488. This gene, GI, as well as the gene encoding a protein-engineered derivative known as GIT, have been described (European Patent Application 351029) and serve as a source for a suitable promoter sequence functional in Streptomyces.

Briefly, plasmid pIJ488-101 was digested with EcoRI and SphI, and the large fragment was isolated and ligated to the GIT gene on an EcoRI-SphI fragment. The resulting plasmid pWGE.GIT was found to be structurally unstable. This instability was attributed to the ermE gene. Therefore the ermE gene was removed from the construct by deletion of the XbaI fragment, resulting in plasmid pWGx.GIT (see FIG. 8).

Plasmid pWGx.GIT was found to still exhibit small segregational instability. A study had been reported describing the replication of the natural Streptomyces plasmid pIJ101 from which all these plasmids were derived (Z. Deng, et al., *Mol. Gen. Genet.* 214:286–294 (1988) In this study, it was demonstrated that pIJ 101 replicates using the "rolling circle" mechanism. Plasmids replicating using this mechanism first synthesize a single-strand intermediate molecule using the known origin of replication, called the plus-origin. Efficient conversion into an active double-strand molecule requires a second origin of replication, called the minus-origin. During the construction of most derivatives of pIJ101, this minus-origin had been removed.

The minus-origin, also called "sti," was isolated from plasmid pIJ211 which is a derivative of pIJ 101, as a KpnI-FspI fragment and ligated into the general cloning vector pTZ18R (Pharmacia, Analects 13, no. 4.). The vector was digested with BamHI and blunted and digested with KpnI. This resulted in plasmid pTZ18Rsti (see FIG. 9).

Plasmid pWGxGIT was digested with KpnI and XbaI. The large fragment was isolated and ligated to the sti-containing fragment isolated from a KpnI and XbaI fragment of pTZ18Rsti. In this manner, plasmid pWGxsGIT was formed (see FIG. 10).

A shuttle-plasmid was constructed by combining plasmids pIJ488-101 and plasmid pWGxsGIT. The fragment containing the Streptomyces replication functions (plus-origin, sti and rep gene) from pWGxsGIT was isolated after digestion with XbaI and SphI. The fragment containing the E. coli replication function was isolated from pIJ488-101 after digestion with XbaI, SphI and NcoI. After ligation of these two fragments, plasmid pIJ488sti was formed (see FIG. 11).

To drive expression of the cellulase, the GI promoter was used together with the signal-sequence of *S. lividans* cellulase, CelA (D. Kluepfel, et al., *Nature Biotechnol.* 14:756–759 (1996). A fusion between the GI-promoter and the CelA signal-sequence was constructed by fusion-PCR techniques, as a XbaI-EcoRI fragment. On the same fragment, a NheI site was introduced for cloning reasons. The fragment was ligated into plasmid pIJ488sti digested with XbaI and EcoRI, resulting in plasmid pIJSEGiCe. (see FIG. 12)

To complete the expression vector, a terminator sequence of cellulase was inserted. Strain Streptomyces 11AG3 is closely related, if not identical, to the Streptomyces strain isolated in Example 1 (11AG8). Both strains were isolated from the same sample, and the sequenced 16S rDNA of the two strains was found to be identical. The 11AG3 cellulase gene was isolated as a NheI-EcoRI PCR-fragment. On the same fragment, a BamHI and a HpaI site were introduced to facilitate cloning. The plasmid pIJSEGiCel was digested with NheI and EcoRI and the PCR-terminator fragment was ligated into the digested plasmid to create vector pIJSEGCi. Next, the cellulase 11AG3 coding region was removed by deletion of the internal BamHI fragment from plasmid pIJSEGCi, resulting in vector pSEGCT (see FIG. 13).

The cellulase 11AG8 gene was isolated from *Streptomyces lividans* TK23 using PCR as a NheI-BamHI fragment. Vector pSEGCT was digested with NheI and BamHI, and the PCR fragment was ligated into the digested vector resulting in plasmid pSEGCT11AG8 (see FIG. 14). The DNA nucleotide sequence of the complete expression cassette consisting of GI-promoter, celA signal-sequence, cellulase 11AG8 and GI-terminator is depicted in FIG. 15, as well as the amino acid sequence of the product (SEQ ID NO:4 and 5).

The host *Streptomyces lividans* TK23 was transformed with plasmid vector pSEGCT11AG8 using the protoplast method described in Hopwood, et al,. GENETIC MANIPU- LATION OF STREPTOMYCES, A LABORATORY MANUAL. The John Innes Foundation, Norwich, United Kingdom (1985).

The transformed culture was expanded to provide two fermentation cultures. At various time points, samples of the fermentation broths were removed for analysis. For purposes of this experiment, the samples were assayed for CMC activity and for molecular weight (SDS-PAGE). At the end of the fermentation run, significant amounts (5–15%) of full length cellulase was observed by SDS-PAGE.

In one of the fermentation runs, full length cellulase rapidly accumulated until about 110.3 hours. From then until 205.5 hours, little more full-length cellulase accumulated and the majority of full length cellulase was processed to a truncated form. In the other fermentation run, the full length cellulase was the dominant cellulase present in the fermenter until about 66.2 hours. After that, truncated forms of cellulase accumulated. Thus, it is likely that in both of these runs, the host cells produced full length cellulase which was then cleaved in the fermenter medium to form the truncated forms of cellulase.

Example 7

Expression of Truncated Actinomycete Cellulase

As found in Example 6, the 35 kD cellulase of the invention when expressed in a *Streptomyces lividans* expression system appears in the extracellular space initially as "full-length" enzyme (from N- to C-terminus: catalytic core, linker region, and cellulose binding domain (CBD) consisting of a total of 340 amino acid residues having a molecular weight of about 35kD, and including 3 disulfide bond bridges. After the fermentation has proceeded for a significant period of time, i.e., about 66 hours, the cellulase is modified by virtue of its cellulose binding domain being clipped off. The resulting "core" molecule retains cellulase activity and has a molecular weight of about 25 kD. An initial cleavage site of the full-length enzyme, if there is one, has not been determined but the precise amino acid sequence (mw) of the core was determined using either purified protein or UF concentrated cell-free broth. From the amino acid sequence an average molecular weight for the truncated protein was calculated.

The sequence identity of the truncated core was determined as follows: An aliquot of 0.2 mg of dissolved enzyme was diluted with chilled water (at least 2 volumes of the sample aliquot) to 0.45 mL, then mixed with 0.05 mL of 1N HCl, and incubated on ice for 10 min. The solution was centrifuged for 2 min at 13,000×g, the supernatant recovered and incubated with 0.065 mL of 50% (w/v) trichloroacetic acid for 10 min on ice. The precipitated protein was recovered by centrifugation, the pellet was washed once with 1 mL of chilled 90% (v/v) acetone and then dissolved in 0.025 mL of 8M urea in 0.5M ammonium bicarbonate. After the pellet had dissolved, 2.5 µL of 0.2M dithiothreitol was added and the solution incubated for 15 min at 50° C. Thereafter, 2.5 µL of 0.44M iodoacetamide in 0.1M ammonium bicarbonate was added and the solution incubated for 15 min in the dark at room temperature. This solution was diluted with 0.1 mL of 0.1% (w/v) n-octyl-β-D-glycoside, and the protein digested with 6 µg of trypsin for 60 min at 37° C. The resulting peptides were separated by RP-HPLC on a $C_{18}$ column and the elution profile was monitored both by UV absorption and mass spectrometry. The assignment of peptides to the given sequence was supported by partial sequencing of 11 out of 13 peaks.

Although the mass determination already provided the information that the "core" consisted of two molecules and of their respective sequence, the C-terminal tryptic peptide mixture was digested with endoproteinase AspN and reanalyzed by LC/MS. The results show that the "core" protein was an approximately 1:2 ratio of two molecules, one with a molecular weight of 24,469.0 Daltons (comprising 230 amino acid residues, 2 disulfide bond bridges) and one with a molecular weight of 24,724.3 Daltons (comprising 233 amino acid residues, 2 disulfide bond bridges). This finding is corroborated by direct mass measurements with a PE Bioscience ESI-TOF mass spectrometer, model Mariner (Foster City, Calif.) which indicated molecular weights of the purified variant core proteins of 24,467.0 and 24,727.6, respectively.

Example 8

Expression of Cellulase via an Alternative Promoter

The GI-promoter has been known to result in very high expression. Because of, e.g., promoter instability, it is possible that high expression of cellulases is not desirable. Thus, an alternative promoter was cloned into the cellulase expression vectors of this invention. The promoter used was the weaker aph promoter of the *Streptomyces fradiae* aminoglycoside 3'-phosphotransferase gene. This promoter was isolated from the plasmid pIJ61, which is a derivative of the natural Streptomyces plasmid SLP1. The complete nucleotide sequence of the aph gene has been known and the promoter region has been characterized.

A fusion-PCR technique was used to obtain a SpeI-NheI fragment containing the aph promoter fused to the celA signal-sequence. The GI-promoter in plasmid pSEGCT11AG8 was then exchanged for the aph promoter by digesting this plasmid with SpeI and NheI, isolating the large fragment, and ligating the PCR-fragment into it. This resulted in plasmid pSEACT11AG8 (see FIG. 16). This plasmid is equivalent to the plasmid pSEGCT11AG8 (see FIG. 14), and can be regarded as to be constructed by insertion of the cellulase from *S. lividens* 11AG8 into a vector pSEACT, which is identical to vector pSEGCT except for the promoter used to drive the expression of the cellulase gene.

To remove all *E. coli* sequences from the plasmid pSEACT11AG8, the plasmid was digested with SphI and religated. This formed plasmid pSACT11AG8 (see FIG. 17). This construct was transfected into a Bacillus host cell. Although high levels of expressed cellulase were observed in plate cultures, production of cellulase by the Bacillus host cells in a fermenter environment was very low. However, it is possible that with better control over promoter induction, production of cellulase under the control of the aph promoter will improve.

Example 9

Comparison of Full Length Cellulase and Truncated Cellulases

A comparison of the depilling performance of full length and truncated cellulase was made.

A three cycle Detergent Cellulase Terg-O-Tometer Test (DCTT) was used to evaluate the dose responses of full length (15.4 mg/mL) and truncated (approximately 14 mg/mL) at 20° C. and 40° C. in Wisk® and Gessy Lever #1 liquid detergents. The experiments were conducted using both prepilled cotton knit swatches and woven cotton swatches. The conditions of the test were:

| | |
|---|---|
| Temperature: | 40° C. |
| Cycle time: | 2.5 hours |
| Number of cycles: | 3 |
| Agitation speed: | 125 |
| Water hardness: | 150 ppm |

| | |
|---|---|
| Enzyme dose: (225 NPC units = 30 mg full length protien) pH liquor: | 0, 45, 90, 135, 180, 225 NPC units/L 8.55 |

The pH was checked before addition of the enzymes and then every 30 minutes during the test.

In performing the 3 cycle test, the swatches were removed from the Terg pot at the end of each cycle, rinsed in the washing machine, then placed back into the Terg pot containing fresh enzyme and detergent. At the end of the 3rd cycle rinse, the swatches were dried in a tumble dryer.

Data Analysis

Depilling: FIG. 18a shows the depilling dose response of full length vs truncated in Wisk® at 40° C. The raw data were fit to the Michaelis-Menten equation and plotted on the graph. These results suggest that there is not a significant difference in the depilling performance of full length vs. truncated in Wisk® at 40° C.

Peak load: FIG. 18b shows the dose response of full length vs truncated in Wisk® at 40° C. Peak load is inversely proportional to strength loss, i.e., the higher the peak load, the lower the TSL. The peak load values are slightly greater in truncated than full length. Thus, although peak load values are slightly lower and TSL greater in truncated than full length, the two enzymes have equal depilling performance.

However, when depilling and %TSL are compared, some differences between the full length and the truncated cellulase are observed. FIG. 18c shows the %TSL vs depilling for full length versus truncated in Wisk® at 40° C. A trendline could be drawn for both full length and truncated showing that as depilling increases TSL increases. This shows that at a depilling rating of 4, truncated has a greater TSL than full length.

In addition to Wisk® liquid detergent, depilling performance was determined in Gessy Lever #1 liquid detergent. Under the same conditions (except for an increase in the pH of the wash to 10.57), the dose responses of full length to truncated were compared at 20° C. and 40° C. in Gessy Lever #1. The pH was checked before enzyme addition and every 30 minutes.

Data Analysis

Depilling: FIG. 19a shows the dose response of full length vs truncated in Gessy Lever #1 @ 20° C. The raw data were fit to the Michaelis-Menten equation and plotted on the graph. As can be seen on the graph, the depilling performance of truncated was better than full length in Gessy Lever #1. In summary, it took 1.6× as much as full length to achieve a depilling rating of two compared to truncated.

Peak Load: FIG. 19b shows the peak load values and TSL of full length vs truncated in Gessy Lever #1 @ 20° C. As expected, the peak load values were greater for truncated than for full length. The scatter in the full length data and low correlation coefficient suggested the enzyme had little effect on the fabric, and therefore caused no TSL. TSL was much lower in Gessy Lever #1 than in Wisk®, most likely due to differences in pH.

To determine the depilling performance in the presence of bleaching agents, the same experiments were performed in the presence of a bleaching system. The conditions of the test were:

| | |
|---|---|
| Temperature: | 40° C. |
| Cycle time: | 2.5 hours |
| Number of cycles: | 3 |
| Agitation speed: | 125 rpm |
| Water hardness: | 70 ppm as CaCO$_3$ (2:1 Ca:Mg) |
| Detergent matrix: | 0.51 grams LAS/0.35 grains STPP/0.68 grams Na$_2$SO$_4$ |
| Bleaching system: | 0.50 grams Perborate monohydrate (PBS)/0.10 grams TAED (bleach activator) |
| pH: | 10 |
| Enzyme doses: | 225 NPC/L full length at 115.6 NPC/mL, (dosed at 30 mg/L) |
| | 225 NPC/L truncated at 149.2 NPC/mL, (dosed at equal act. to full length) |
| | 34 NPC/L "Super L" EGIII @ 23 NPC/mL, (dosed at 30 mg/L) |

The pH was adjusted both before and after enzyme dosing, then checked every 30 minutes and adjusted as needed.

Data Analysis

Depilling: FIG. 20a shows the depilling performance of full length, truncated and EGIII in an alkaline detergent matrix ± an oxygen bleaching system. As can be seen on the graph, with the addition of PBS/TAED, depilling decreased in all three enzymes. The full length and EGIII was the most affected in the presence of the bleaching system. The truncated had the best depilling performance even in the presence of an oxygen bleaching system with a depilling rating of 3.5. This data suggest that truncated is more stable than full length and EGIII in the presence of the bleaching system.

Peak Load: FIG. 20b shows peak load values of full length, truncated and EGIII in an alkaline detergent matrix ± an oxygen bleaching system. As can be seen, the peak load values were the same for full length and EGIII in the presence of an bleaching system, while the peak load values increased for truncated. TSL was found to be inversely proportional to peak load. The peak load values for truncated increased in the presence of the bleaching system, thus TSL decreased.

In addition to bleach, laundry detergents may contain proteases. Thus, the experiments described above were performed with Purafect 4000L® (Genencor, International) present. The conditions of the test were:

| | |
|---|---|
| Temperature: | 40° C. |
| Cycle time: | 2.5 hours |
| Number of cycles: | 3 |
| Agitation speed: | 125 rpm |
| Water hardness: | 70 ppm as CaCO$_3$ (2:1 Ca:Mg) |
| Detergent matrix: | 0.51 grams LAS/0.35 grams STPP/0.68 grams Na$_2$SO$_4$ |
| Protease: | 1 mg/L Purafect 4000L ® |
| pH: | 10 |
| Enzyme doses: | 225 NPC/L full length at 115.6 NPC/ml, (dosed at 30 mg/L) |
| | 225 NPC/L truncated at 149.2 NPC/ml, (dosed at equal act. to full length) |
| | 34 NPC/L "Super L" BGIII at 23 NPC/ml, (dosed at 30 mg/L) |

Data Analysis

Depilling: FIG. 21a shows the depilling performance of full length, truncated and EGIII in an alkaline detergent matrix ± Purafect 4000L® protease. The no cellulase control ± Purafect 4000L had no depilling performance. The depilling performance of full length increased in the presence of Purafect 4000L®, while the performance of the truncated was unchanged. This suggested the truncated is more proteolytically stable than the full length enzyme. The performance of the full length +Purafect 4000L® increased to the same performance level of the truncated. This observation agrees with earlier observations that truncated performs better than full length under alkaline conditions. The performance of EGIII is unaffected by the presence of Purafect 4000L® protease.

Peak Load: FIG. 21b shows the peak load values of full length, truncated and EGIII in an alkaline detergent matrix ± Purafect 4000L® protease. The addition of Purafect 4000L to the null control had no effect on peak load values. The peak load values for full length decreased in the presence of Purafect 40001L®, meaning TSL increased in the presence of protease. Because TSL is inversely proportional to peak load, as the depilling of full length increased upon addition of Purafect 4000®, TSL increased as well. Once again, protease had little or no effect on the truncated. The peak load values for EGIII remained unaffected in the presence of Purafect 4000L.

What is claimed is:

1. An isolated truncated cellulase having cellulolytic activity comprising a contiguous amino acid sequence that is at least 90% identical to an amino acid sequence that corresponds to about position 31 and extends to about position 261 of SEQ ID NO: 1.

2. The truncated cellulase according to claim 1, wherein said cellulase is obtainable from an Actinomycete.

3. The truncated cellulase according to claim 1, wherein said truncated cellulase comprises a contiguous amino acid sequence that corresponds to about position 31 and extends to about position 261 of SEQ ID NO: 1.

4. An isolated cellulase comprising a fragment of a full-length cellulase, wherein the full-length cellulase is at least 90% identical to the amino acid sequence provided in SEQ ID NO: 1 and is cleaved to form the fragment, said fragment having cellulolytic activity and a molecular weight of about 25 kD.

5. A detergent composition comprising the cellulase according to claim 1.

6. A detergent composition comprising the cellulase according to claim 4.

7. An animal feed additive comprising the truncated cellulase according to claim 1.

8. An animal feed additive comprising the cellulase according to claim 4.

9. A composition comprising the truncated cellulase according to claim 1, wherein said composition is used for the treatment of textiles.

10. A composition comprising the cellulase according to claim 4, wherein said composition is used for the treatment of textiles.

11. A composition comprising the truncated cellulase according to claim 1, wherein said composition is used for the treatment of pulp and paper.

12. A composition comprising the cellulase according to claim 4, wherein said composition is used for the treatment of pulp and paper.

* * * * *